United States Patent
Alt et al.

(10) Patent No.: US 8,951,513 B2
(45) Date of Patent: Feb. 10, 2015

(54) METHODS AND APPARATUS FOR ENHANCED RECOVERY OF CELLS AND OF CELL-ENRICHED MATRIX FROM TISSUE SAMPLES

(75) Inventors: Eckhard U. Alt, Houston, TX (US); Michael E. Coleman, Houston, TX (US); Ron Stubbers, Houston, TX (US)

(73) Assignee: Ingeneron Incorporated, Houston, TX (US)

( * ) Notice: Subject to any disclaimer, the term of this patent is extended or adjusted under 35 U.S.C. 154(b) by 0 days.

(21) Appl. No.: 13/329,143

(22) Filed: Dec. 16, 2011

(65) Prior Publication Data

US 2012/0195863 A1 Aug. 2, 2012

Related U.S. Application Data

(63) Continuation-in-part of application No. 13/385,599, filed on Nov. 3, 2011, now abandoned.

(60) Provisional application No. 61/424,012, filed on Dec. 16, 2010.

(51) Int. Cl.
| | |
|---|---|
| *A61K 35/12* | (2006.01) |
| *B04B 5/04* | (2006.01) |
| *B04B 15/02* | (2006.01) |
| *C12N 5/0775* | (2010.01) |
| *C12M 1/00* | (2006.01) |

(52) U.S. Cl.
CPC ............... *B04B 5/0414* (2013.01); *B04B 15/02* (2013.01); *C12N 5/0667* (2013.01); *C12M 47/02* (2013.01)
USPC ....................................................... 424/93.7

(58) Field of Classification Search
USPC ....................................................... 424/93.7
See application file for complete search history.

(56) References Cited

U.S. PATENT DOCUMENTS

| | | | |
|---|---|---|---|
| 2003/0082152 A1* | 5/2003 | Hedrick et al. | 424/93.21 |
| 2008/0014181 A1* | 1/2008 | Ariff et al. | 424/93.7 |
| 2009/0035283 A1* | 2/2009 | Park et al. | 424/93.7 |
| 2010/0124563 A1 | 5/2010 | Coleman et al. | |
| 2010/0285588 A1 | 11/2010 | Stubbers et al. | |

FOREIGN PATENT DOCUMENTS

| | | | | |
|---|---|---|---|---|
| EP | 1699548 | * | 6/2008 | B01F 13/00 |
| WO | WO0053795 | * | 9/2000 | C12Q 1/00 |
| WO | WO2009120879 | * | 10/2009 | C12N 5/08 |

OTHER PUBLICATIONS

Kubota. Multi-purpose table top centrifuge. Kubota Corporation. 2004;1-4.*
Alt et al., "Effect of freshly isolated autologous tissue resident stromal cells on cardiac function and perfusion following acute myocardial infarction," *International J of Cardiology*, 2009, 10 pages.
Altman et al., "Adhesion, Migration, and Mechanics of Human Adipose Tissue Derived Stem Cells on Silk Fibroin-Chitosan Matrix," *Acta Biomaterialia*, 2009, 41 pages.
Altman et al., "Adipose Tissue-Derived Stem Cells Enhance Bioprosthetic Mesh Repair of Ventral Hernias," *Plast. Reconst. Surg.*, 2010, 126:1-10.
Altman et al., "Dermal matrix as a carrier for in vivo delivery of human adipose-derived stem cells," *Biomaterials*, 2008, 29:1431-1442.
Altman et al., "Human Adipose-Derived Stem Cells Adhere to Acellular Dermal Matrix," *Aesth Plast Surg*, 2008, 32:698-699.
Altman et al., "Human Tissue-Resident Stem Cells Combined with Hyaluronic Acid Gel Provide Fibrovascular-Integrated Soft-Tissue Augmentation in a Murine Photoaged Skin Model," *Plast. Reconst. Surg.*, 2010, 125:1-12.
Altman et al., "IFATS Collection: Human Adipose-Derived Stem Cells Seeded on a Silk Fibroin-Chitosan Scaffold Enhance Wound Repair in a Murine Soft Tissue Injury Model," *Stem Cells*, 2009, 27:250-258.
Altman et al., "Magnetic resonance imaging as a novel method of characterization of cutaneous photoaging in a murine model," *Arch Dermatol Res*, 2008, 5 pages.
Bai et al., "Both cultured and freshly isolated adipose tissue-derived stem cells enhance cardiac function after acute myocardial infarction," *European Heart J Advance Access*, 2009, 1-13.
Bai et al., "Electrophysiological properties of human adipose tissue-derived stem cells," *Am. J. Physiol Cell Physiol.*, 2007, 293:C1539-C1550.
Bai et al., "Genetically selected stem cells from human adipose tissue express cardiac markers," *Biochem and Biophysical Res. Comm.*, 2007, 353:665-671.
Bai et al., "Tracking Long-Term Survival of Intramyocardially Delivered Human Adipose Tissue-Derived Stem Cells Using Bioluminescence Imaging," *Mol Imaging and Bio*, 2010, 14 pages.
Bai et al., "VEGF receptor Flk-1 plays an important role in c-kit expression in adipose tissue derived stem cells," *FEBS Letters*, 2007, 581:4681-4684.
Droll et al., "TNFα protects tissue resident stem cells $H_2O_2$ induced apoptosis through a novel NF-κB p50/p50 homodimer mediated signaling pathway," *Biochem and Biophysical Res. Comm.*, 2008, 371:626-629.
Fotuhi et al., "Electrophysiological consequence of adipose-derived stem cell transplantation in infarcted porcine myocardium," *European Society of Cardiology*, 2007, 9:1218-1221.
Gehmert et al., "Breast cancer cells attract the migration of adipose tissue-derived stem cells via the PDGF-BB/PDGFR-β signalling pathway," *Biochem and Biophysical Res. Comm.*, 2010, 398:601-605.

(Continued)

*Primary Examiner* — Ruth Davis
*Assistant Examiner* — Lynn Y Fan

(57) ABSTRACT

This document describes methods and an apparatus for recovery of a cell-enriched matrix and cells (e.g., regenerative cells) from a tissue sample. In some embodiments, at least two rounds of acceleration and deceleration are performed.

19 Claims, 16 Drawing Sheets

(56) References Cited

OTHER PUBLICATIONS

Kurita et al., "Influences of Centrifugation on Cells and Tissues in Liposuction Aspirates: Optimized Centrifugation for Lipotransfer and Cell Isolation," *Plast. Reconst. Surg.*, 2008, 121:1033-1041.

Metzele et al., "Human adipose tissue-derived stem cells exhibit proliferation potential and spontaneous rhythmic contraction after fusion with neonatal rat cardiomyocytes," *FASEB J*, 2010, 25:1-10.

Sadat et al., "The cardioprotective effect of mesenchymal stem cells is mediated by IGF-I and VEGF," *Biochem and Biophysical Res. Comm.*, 2007, 363:674-679.

Song et al., "VEGF is critical for spontaneous differentiation of stem cells into cardiomyocytes," *Biochem and Biophysical Res. Comm.*, 2007, 354:99-1003.

Valina et al., "Intracoronary administration of autologous adipose tissue-derived stem cells improves left ventricular function, perfusion, and remodeling after acute myocardial infarction," *European Heart Journal*, 2007, 28:2667-2677.

Zhang et al., "Chemoprevention of colorectal cancer by targeting APC-deficient cells for apoptosis," *Nature*, 2010, 6 pages.

\* cited by examiner

METHODS AND APPARATUS FOR ENHANCED RECOVERY OF CELLS AND OF CELL-ENRICHED MATRIX FROM TISSUE SAMPLES

CROSS-REFERENCE TO RELATED APPLICATIONS

This application claims priority to U.S. Provisional Application No. 61/424,012, filed Dec. 16, 2010, now expired, and to U.S. Provisional Application No. 61/555,305, filed Nov. 3, 2011, which was converted to U.S. Nonprovisional Application No. 13/385,599, now abandoned, and is a continuation-in-part of both the '012 provisional application and the '599 nonprovisional application. The disclosures of the prior applications are considered part of (and are incorporated in their entireties by reference in) the disclosure of this application.

TECHNICAL FIELD

This invention relates to methods and an apparatus for recovery of a cell-enriched matrix and recovery of cells, and more particularly to recovery of cells from a tissue sample using two or more acceleration and deceleration steps under centrifugal force, and combinations thereof.

BACKGROUND

Current strategies in regenerative medicine aim towards replacing tissue that undergoes an increased apoptosis rate. That means that within the organ there is a net loss of functional cells because more cells are dying than are being replaced. Therefore, the transfer of regenerative cells, e.g., stem cells and progenitor cells, from one location to the site of renewal is a therapeutic approach to restore the organ back to an equilibrium. Research at our laboratories has shown that stem cells and regenerative cells are present in every organ, primarily located in the vascular and perivascular space with the early progenitor cells in the vessel wall attached to the lamina elastica interna. One population of these cells is able to replace the stroma of an organ, the other part of these cells is capable to differentiate into the respective parenchym of the specific organ. Each organ can be compared to a house, where the stroma made from fibroblasts and consisting of extracellular matrix can be compared to walls of bricks and mortar in a house, the piping in a house corresponds to blood vessels of the organ and nerves represent the electrical wiring in the walls. Inside these houses, in each organ one has a certain type of inhabitants, such as liver cells, heart cells, bone cells, cartilage or fat cells, also called the parenchym of an organ.

In order to restore function to a dysfunctional organ, it is important to provide both the stroma, that means the housing that form the walls of the organ and the inhabitants, which are the specific parenchymal cells.

A simple means to recover the regenerative cells capable of restoring organ function is to dissociate them from subcutaneous fat tissue, because it is rich in blood vessels and the removable adipose tissue is not essential for life. Most people are capable, even happy, to donate several grams of those tissues.

Autologous grafting of tissue harvested by lipoaspiration is a common procedure in cosmetic surgery for both small (e.g., nasolabial folds) and large (buttocks or breast) volume filling applications. The primary benefits of this procedure termed "autologous fat grafting" are lower cost versus synthetic fillers and no immune rejection since the patient's own tissue is used. Currently, multiple methods of lipoaspirate collection and processing are employed to obtain tissue for grafting. Factors that determine clinical outcomes following autologous fat grafting have not been fully elucidated. However, it is widely recognized that improving the persistence of the graft is an area of significant need.

SUMMARY

Transferred fat tissue or adipose cells recovered from one location in the body and transferred to another continue to have an aerobic metabolism. Without adequate blood supply these cells undergo necrosis, apoptosis, and autophagy within 24 to 48 hours and die. The problem with traditional fat grafting, where fat is taken out by liposuction from one location in the body and re-injected at another location, is that a great fraction of cells transferred do not survive and the dying cells can cause considerable local inflammation. Persistence and regenerative potential of the fat graft is not correlated with the content of lipid-filled adipocytes in the graft, but instead with the content of regenerative cells such as stem cells and with the administered extracellular matrix. Post-grafting loss of mature adipocytes is high due to the trauma of harvest and re-administration and to the ischemic nature of the graft environment. In contrast, stem and regenerative cells are more resistant to these factors and thus contribute substantially to long term graft viability and regenerative potential.

The present document is based on an improved method for volume filling of subcutaneous tissue or other connective tissue structures that need a volume build up. The method includes transfer of a cell-enriched matrix that has a reduced lipid content, but an increased concentration of regenerative cells. It is known that connective tissue has a considerably long tolerance to ischemia since it has a significantly lower metabolism compared to adipocytes cells. Therefore it is the aim of the present invention to provide method and apparatus for a long-term stable volume filling with a cell-cell-enriched matrix. This results in greater survival of the tissue when it is transplanted to a new location. Accordingly as described herein, neovascularization from the tissue resident stem cells provides a greater viability of the transplanted graft. An additional improvement to this method is to re-apply a mixture of the cell-enriched matrix together with dissociated regenerative cells recovered by the method described herein that includes enzymatic dissociation of lipoaspirate in a heated centrifuge by acceleration and deceleration in an inverted rotor.

Accordingly, the present document provides novel methods for preparation and recovery of a cell-enriched matrix, improved recovery of regenerative cells from their subcutaneous location by means of the same apparatus as used for the recovery of the matrix, and the combination of cell-enriched matrix and regenerative cells for enhanced neovascularization and better survival of the transplanted volume filling graft tissue.

The present document also provides provide cost effective means for recovery of regenerative cells, which are defined as early mesenchymal cells plus the whole range of progenitor cells, from their location in subcutaneous adipose tissue. Pre-processing and reducing the content of lipid-filled cells from the initial lipoaspirate is an effective method to save costly enzymes such as collagenase and neutral protease. The methods include a two-step approach where the amount of lipid-filled cells in the lipoaspirate is reduced and a cell-enriched matrix is recovered, and then subjecting the cell-enriched matrix with reduced lipid content to an enzymatic and mechanical process by using also increased temperature from a heated centrifuge with a reconfigurable rotor and repeated cycles of acceleration and deceleration to recover a regenerative cellular preparation at optimized cost.

Currently known methods to process subcutaneous fat with the aim to obtain a processed lipoaspirate apply just centrifugation. As shown herein, processing by centrifugation alone can increase the cellular yield of processed tissue. However, extruding the adipose tissue before the centrifugation step significantly increases the cellular content of the processed lipoaspirate material, referred to as the cell-enriched matrix.

Processing of subcutaneous tissue can be performed as described herein to yield a cell-enriched matrix, which primarily consists of collagen, laminin, elastin and other proteoglycans of the extracellular matrix and tissue resident cells, including stem and progenitor cells, collectively "regenerative cells" or "regenerative platform," still bound in the tissue. Typically, a cell-enriched matrix contains 90% or more of the regenerative cells bound in their tissue location.

In one embodiment, the present document provides methods and an apparatus for preparing and recovering a cell-enriched matrix.

In one embodiment, the present document provides methods and an apparatus for preparing and recovering regenerative cells from the cell-enriched matrix.

In one embodiment, cellular compositions are provided that include regenerative cells isolated as described herein, or cellular compositions containing both a cell-enriched matrix and regenerative cells. The cell-enriched matrix prepared as described herein has a reduced lipid content, but an increased concentration of regenerative cells. It is known, that connective tissue has a considerably long tolerance to ischemia since it has a significantly lower metabolism compared to adipocytes cells. Cellular compositions described herein can enhance neovascularization of grafts and increase long term survival of the graft. Cellular compositions containing a combination of the cell-enriched matrix and regenerative cells are particularly useful for enhancing neovascularization of grafts and increasing long term survival of the graft.

In one embodiment, this document features a method for recovering cell-enriched matrix from tissue. The method includes extruding a tissue sample that contains a suspension of adipose tissue pieces in an aqueous fluid through an ostium and centrifuging the extruded tissue sample to isolate a cell-enriched matrix. The ostium can be from 1 to 5 mm in diameter. The extruded tissue sample is centrifuged for at least five minutes at a minimum of 400×g, preferably at higher g force up to 1200×g (e.g., 400×g to 1200×g). Cells can be recovered from the cell-enriched matrix as described herein.

In another aspect, this document features a method for recovering cells from tissue. The method includes providing an extruded tissue sample housed in a container adapted for a centrifuge, the tissue sample comprising a suspension of tissue pieces in an aqueous fluid; subjecting the sample to at least one acceleration and deceleration step using centrifugal force applied through a rotating element, wherein the rotating element comprises a shaft and one or more arms that extend from the shaft, wherein (i) the one or more arms are supported from the shaft in such a manner that when the shaft rotates, the one or more arms swing upward and outward relative to the shaft or (ii) the one or more arms are supported at a fixed angle, wherein the containers attached to said arms are held in such a position that gravitational force on material is opposite of applied centrifugal force, wherein said applied centrifugal force ranges from about 50 g to about 4000 g. The temperature of the sample can be maintained between 32° and 42° C. One or more enzymes (e.g., proteases such as collagenases or neutral proteases, or other enzymes as described herein) also can be included.

In one embodiment, this document features a method for recovering a regenerative platform from a tissue sample (e.g., lipoaspirate, adipose tissue, and combinations thereof). The method includes providing a tissue sample housed in a first tissue collection container adapted for an automated tissue processing unit, wherein the automated tissue processing unit comprises a removable rotating apparatus comprising at least two cavities, wherein each cavity is configured for detachably inserting a tissue collection container within the cavity wherein the tissue sample comprises a suspension of tissue pieces in an aqueous fluid; and subjecting the tissue sample to at least one round of centrifugation of at least 400×g for at least about 5 minutes using the automated tissue processing unit, thereby separating a cell-enriched matrix from the tissue sample, wherein the cell-enriched matrix comprises a regenerative platform. The method further can include extruding the tissue sample through an orifice prior to placing the tissue sample into the automated tissue processing unit. The cell-enriched matrix can have a higher concentration of the regenerative platform compared to an otherwise corresponding method absent the extruding the tissue sample through an orifice. The method further can include transferring the tissue sample concentrate from the first tissue collection container into a second collection container by a closed system method. In some embodiments, at least one protease can be added to the second collection container. The cell-enriched matrix can be subjected to at least two rounds of acceleration, wherein each round of acceleration is followed by a round of deceleration, thereby disaggregating the cell-enriched matrix. In some embodiments, the cell-enriched matrix can be filtered to obtain an injectable regenerative platform.

In any of the methods described herein, the method further can include administering at least a portion of the injectable regenerative platform into a subject at an injection site, whereby the injection alters an area at or near the injection site.

This document also features a method for disaggregating a cell-enriched matrix having a regenerative platform therein, wherein the method comprises providing a cell-enriched matrix housed in a second tissue collection container adapted for an automated tissue processing unit, wherein the tissue collection container comprises at least one protease; and subjecting the cell-enriched matrix to at least two rounds of acceleration, wherein each round of acceleration is followed by a round of deceleration, and wherein at least two rounds of acceleration and deceleration are performed at a rate of at least 10×g thereby disaggregating the cell-enriched matrix. The method further can include filtering, or filtering and concentrating, the disaggregated cell-enriched matrix to obtain an injectable regenerative platform.

This document also features a removable rotating apparatus comprising at least two cavities, wherein each cavity is configured for detachably inserting a tissue collection container within the cavity, wherein the removable rotating apparatus is configured to rotate within an automated tissue processing unit for separating a cell-enriched matrix from a tissue sample. The removable rotating apparatus can include a radio-frequency identification (RFID) tag attached thereto that allows the removable rotating apparatus to be identified by the automated tissue processing unit. Alternatively, the type of removable rotating apparatus may be identified based on the amount of electrical current required to accelerate the apparatus during the acceleration phase. The removable rotating apparatus can include autoclavable materials.

In another aspect, this document features an automated tissue processing unit for isolating a cell-enriched matrix from a tissue sample. The automated tissue processing unit can include a removable rotating apparatus comprising at least two cavities, wherein each cavity is configured for detachably inserting a tissue collection container within the cavity. The automated tissue processing unit can include a temperature control device. The automated tissue processing unit can be configured to have at least two stop-start intervals of acceleration. The removable rotating apparatus can have at least one pre-determined specification that allows the automated tissue processing unit to identify the removable rotating apparatus.

In another aspect, a modified centrifuge is provided that can be used to perform at least two series of rapid acceleration and deceleration steps under centrifugal force. Such steps can be performed in a thermally regulated environment (e.g., 35-42° C.) in the presence of one or more enzymes (e.g., a collagenase and a neutral protease) to enhance the degradation of the extracellular matrix and release of cells. Centrifugation can be used to recover cells released from the extracellular matrix. The methods and apparatus described herein can be used to process any human or animal tissue that contains blood vessels. The methods and apparatus are particularly useful for recovering cells from adipose tissue (e.g., subcutaneous or intra-abdominal adipose tissue), which is rich in vascularization and easy to recover from a subject.

This document also provides a method for recovering cells from tissue. The method includes providing a tissue sample housed in a container adapted for a centrifuge, the tissue sample including a suspension of tissue pieces in an aqueous fluid; and subjecting the tissue sample to a plurality of acceleration and deceleration steps using centrifugal force. The tissue sample can include human tissue or animal tissue, and can contain blood vessels. The tissue sample can be adipose tissue such as lipoaspirate. The method can include maintaining a temperature of from 26° C. to 42° C. inside the container while subjecting the tissue sample to the plurality of acceleration and deceleration steps. The tissue sample can be subjected to the plurality of acceleration and deceleration steps in the presence of one or more enzymes (e.g., a collagenase, other protease, or a mixture thereof).

In some embodiments, each of the acceleration steps can be performed for 5 to 20 seconds and each of the deceleration steps can be performed for 3 to 20 seconds. The tissue sample can be subjected to the plurality of acceleration and deceleration steps for 5 minutes to 180 minutes (e.g., 20 minutes to 60 minutes). In one embodiment, the tissue sample is subjected to at least three cycles of acceleration to 200×g and deceleration to 1×g per minute for 30 minutes.

In another aspect, this document features a method for recovering cells from tissue. The method includes providing a tissue sample housed in a container adapted for a centrifuge, the tissue sample including a suspension of tissue pieces in an aqueous fluid; subjecting the sample to a plurality of acceleration and deceleration steps using centrifugal force applied through a rotating element, wherein the rotating element comprises a shaft and one or more arms that extend from the shaft, wherein (i) the one or more arms are supported from the shaft in such a manner that when the shaft rotates, the one or more arms swing upward and outward relative to the shaft or (ii) the one or more arms are supported at a fixed angle, wherein the containers attached to the arms are held in such a position that gravitational force on material is opposite of applied centrifugal force, wherein the applied centrifugal force ranges from about 50 g to about 4000 g. Each of the acceleration steps can be performed for 5 to 20 seconds. Each of the deceleration steps can be performed for 3 to 20 seconds.

The tissue sample can be subjected to the plurality of acceleration and deceleration steps for 5 minutes to 180 minutes (e.g., 20 minutes to 60 minutes). In one embodiment, the tissue sample is subjected to at least three cycles of acceleration to 200×g and deceleration to 1×g per minute for 30 minutes.

This document also features a method for recovering regenerative cells from tissue. The method includes providing a tissue sample housed in a container adapted for a centrifuge, the tissue sample comprising a suspension of tissue pieces in an aqueous fluid; subjecting the sample to a plurality of acceleration and deceleration steps using centrifugal force; and centrifuging the sample at 400 to 4000×g to isolate cellular components. The sample, when subjected to centrifugation at 400 to 4000×g, can be housed within a container that includes an elongated cylindrical central portion; a first end portion integrally formed with the central portion; and a second open end portion integrally formed with the central portion, wherein the first end portion narrows down to a narrow opening, and comprises a collection portion protruding from the end portion at the narrow opening, wherein the collection portion is capable of receiving and storing a liquid and comprises a removable plug to seal the first end portion from the collection portion.

In any of the methods described herein, the container can include a porous insert, wherein the porous insert is composed of a biocompatible material and having a pore size ranging from 0.5 mm to 5 mm, wherein the porous insert enhances the dissociation of cells from the extracellular matrix of the tissue sample when the tissue sample is subjected to said plurality of acceleration and deceleration steps. The porous insert can be substantially cylindrical in shape, an inverted substantially conical shape, or can bisect the container into upper and lower portions.

In any of the methods described herein, the container can include a plurality of particles, wherein the particles are at least 100 micrometer in diameter and composed of one or more biocompatible materials, wherein the particles enhance the dissociation of cells from the extracellular matrix of the tissue sample when the tissue sample is subjected to the plurality of acceleration and deceleration steps. The plurality of particles can include particles of different specific gravities or shapes.

In any of the methods described herein, the container can include a shaft disposed vertically in the internal lumen of the container, the shaft further including a plurality of arms disposed along a length of the shaft and extending substantially radially from the shaft into the lumen of the container, wherein the arms enhance the dissociation of cells from the extracellular matrix of the tissue sample when the tissue sample is subjected to the plurality of acceleration and deceleration steps. The arms can be of different shapes or sizes. The container can include a removable lid, wherein the shaft is affixed to the removable lid. The shaft can be rotatably affixed to the container. The shaft can be moveable within the lumen of the container.

In another aspect, this document features a container or container assembly that includes an elongated cylindrical central portion; a first end portion integrally formed with the central portion; a second open end portion integrally formed with the central portion; and a port extending radially outward from the elongated cylindrical portion, wherein the first end portion narrows down to a narrow opening, and includes a collection portion protruding from the end portion at the narrow opening, wherein the collection portion is capable of receiving and storing a fluid and comprises a removable plug to seal the first end portion from the collection portion. The removable plug can allow fluid to flow from the end portion into the collection portion upon centrifugal force, pressure, dissociation with an enzyme, or physical removal. The collection portion can be detachable from the first end portion. The collection portion can include an aqueous fluid. The second open end includes a mating portion.

This document also features a container assembly that includes a first container; a second container; and a coupling device adapted to couple the first container to the second container. The first container is described above. The second container includes an elongated cylindrical central portion, a closed end portion integrally formed with the central portion, and an open end portion integrally formed with the central portion, wherein the open end portion of the second container comprises a mating portion; and the coupling device comprising a tubular central portion with first and second open ends and a porous insert extending horizontally across the coupling device, wherein each open end of the coupling device comprises a mating portion, wherein the porous insert has a pore size of 40 to 500 μm. The coupling device further includes a port extending radially outward from the tubular central portion, wherein one mating portion of the coupling device is attached to the mating portion of the first container and the other mating portion of the coupling device is attached to the mating portion of the second container. The port can include a porous insert.

The first and second containers can be pre-assembled, wherein an interior space defined by the first container and the second container is at least partially under vacuum.

This document also features a container that includes an elongated cylindrical central portion defining an internal lumen; a first end portion integrally formed with the central lumen; a second open end portion integrally formed with the central portion; a shaft disposed vertically in the internal lumen; and a plurality of arms disposed along a length of the shaft and extending in a substantially radial direction from the shaft into the internal lumen. The plurality of arms can be of different shapes or sizes. The container further can include a removable lid that attaches to the second open end portion, wherein the shaft is affixed to the removable lid. The shaft can be rotatably affixed to the container. The shaft can be moveable within the lumen of the container.

In another aspect, this document features a kit that includes any of the containers or container assemblies described herein. The kit further one or more cell separation reagents.

In another aspect, this document features a method to increase the cellular content in a processed lipoaspirate with the aim to recover a cell enriched matrix for re-application to a patient, the method includes extruding the lipoaspirate through an orifice of a defined diameter in the range of 1-5 mm, and then subjecting the extruded lipoaspirate to a continuous centrifugation step of at least five minutes and a g-force of a minimum of 400×g. The centrifugation step can include centrifugal force of up to 2000×g. The centrifugation step can include centrifugal force of about 1200×g. The tissue sample can include lipoaspirate, adipose tissue, and combinations thereof. The centrifugation can be performed using a fixed angle, horizontal rotor.

In another aspect, this document features a method of facilitated recovery of regenerative cells from adipose tissue comprising accelerating and decelerating the tissue in the presence of proteolytic enzyme within a centrifuge, whereby the container for the tissue is inverted. The interior of the centrifuge can be temperature controlled. One or more cycles per minute of acceleration and deceleration can be applied to the tissue. The proteolyic enzyme can be a collagenase, a neutral protease or both. A combination of collagenase and a neutral protease can be used together with increased temperature and agitation by centrifugal acceleration and deceleration in an inverted rotor for facilitated recovery of regenerative cells from adipose tissue.

This document also features a method of cost effective recovery of regenerative cells from adipose tissue comprising providing a cell enriched matrix; accelerating and decelerating the cell-enriched matrix in the presence of proteolytic enzyme within a centrifuge, whereby the container for the tissue is inverted. The interior of the centrifuge can be temperature controlled. One or more cycles per minute of acceleration and deceleration can be applied to the cell-enriched matrix. A combination of collagenase and a neutral protease can be used together with increased temperature and agitation by centrifugal acceleration and deceleration in an inverted rotor for facilitated recovery of regenerative cells from cell-enriched matrix.

This document also features a composition containing a cell-enriched matrix prepared as described herein together with a regenerative cell preparation prepared as described herein for injection into a patient.

In another aspect, this document features a removable rotating apparatus comprising at least two cavities, wherein each cavity is configured for detachably inserting a tissue collection container within the cavity, wherein the removable rotating apparatus is configured to rotate within an automated tissue processing unit for separating a cell enriched matrix from a tissue sample. The removable rotating apparatus comprises a radio-frequency identification (RFID) tag attached thereto that allows the removable rotating apparatus to be identified by the automated tissue processing unit. The removable rotating apparatus can include autoclavable materials.

This document also features an automated tissue processing unit for isolating a cell enriched matrix from a tissue sample, wherein the automated tissue processing unit comprises a removable rotating apparatus comprising at least two cavities, wherein each cavity is configured for detachably inserting a tissue collection container within the cavity. The automated tissue processing unit comprises a temperature control device. The removable rotating apparatus has at least one pre-determined specification that allows the automated tissue processing unit to identify the removable rotating apparatus.

In another aspect, this document features a method for recovering cells from adipose tissue. The method including extruding lipoaspirate through an ostium; centrifuging the extruded lipoaspirate to produce a cell enriched matrix; and subjecting thecell enriched matrix to a plurality of acceleration and deceleration steps using centrifugal force to recover regenerative cells from the cell enriched matrix. The method further can include maintaining a temperature of from 26° C. to 42° C. inside the container while subjecting the tissue sample to the plurality of acceleration and deceleration steps. The tissue sample can be subjected to the plurality of acceleration and deceleration steps in the presence of one or more enzymes (e.g., a collagenase, other protease, or a mixture thereof).

In another aspect, this document features a method for recovering cells from tissue. The method includes providing a tissue sample housed in a container adapted for a centrifuge, the tissue sample comprising a suspension of tissue pieces in an aqueous fluid; subjecting the sample to at least one acceleration and deceleration step using centrifugal force applied through a rotating element, wherein the rotating element comprises a shaft and one or more arms that extend from the shaft, wherein (i) the one or more arms are supported from the shaft in such a manner that when the shaft rotates, the one or more arms swing upward and outward relative to the shaft or (ii) the one or more arms are supported at a fixed angle, wherein the containers attached to said arms are held in such a position that gravitational force on material is opposite of applied centrifugal force, wherein said applied centrifugal force ranges from about 50 g to about 4000 g. The temperature of the sample can be maintained between 32° and 42° C. The tissue sample further can include one or more proteases.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, Genbank® Accession Nos, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

BRIEF DESCRIPTION OF DRAWINGS

Like reference symbols in the various drawings indicate like elements.

DETAILED DESCRIPTION

Figure 1:
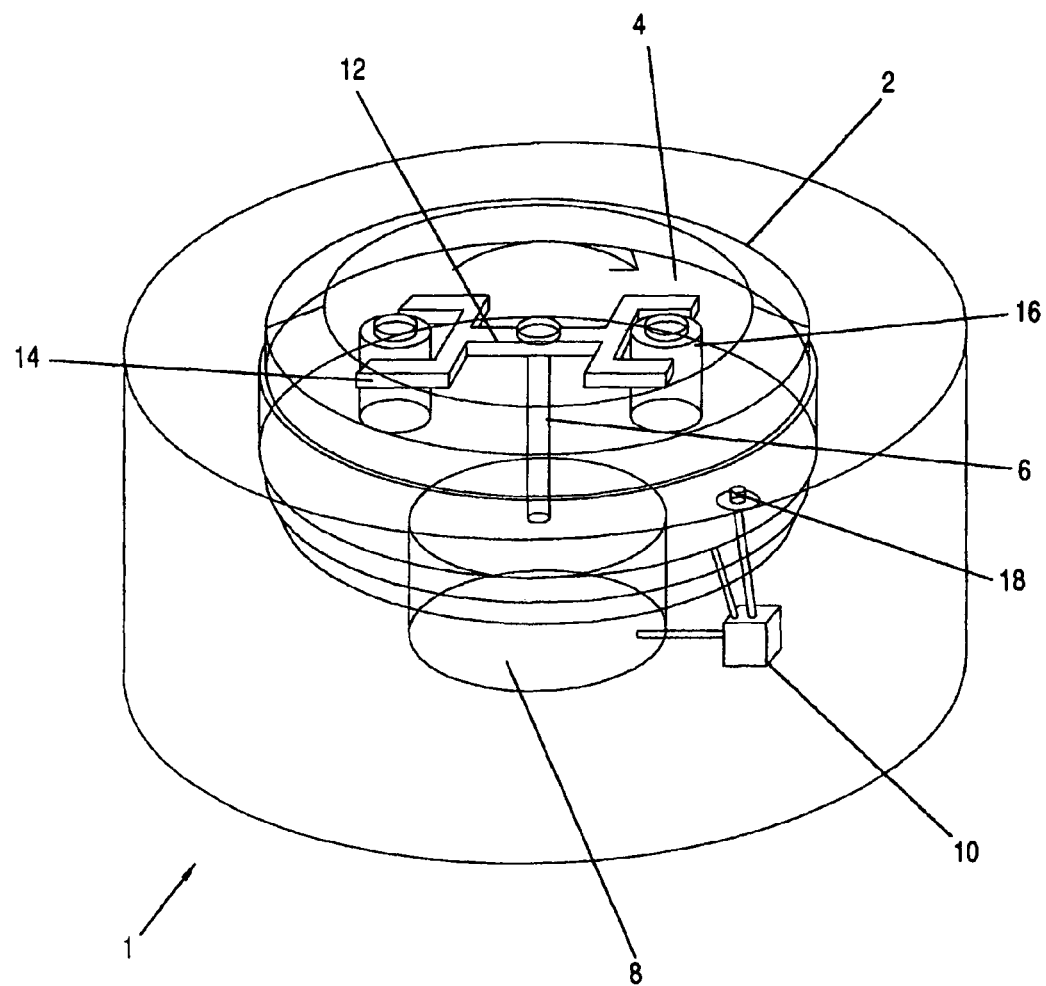
FIG. 1 is a perspective view of an apparatus for dissociation, separation and recovery of cells from a tissue sample according to an embodiment described herein.

In general, this document is based on methods and apparatus for recovery of cells from tissues, including human and animal tissues such as canine, feline, equine, bovine, ovine, or porcine tissues. The methods and apparatus described herein are particularly useful for recovery of cells from adipose tissue obtained from, for example, liposuction (i.e., lipoaspirate), including suction assisted, vapor assisted, or ultrasound assisted liposuction, and combinations thereof. For instance, the methods and apparatus described herein can be used to isolate stem cells, progenitor cells, hematopoietic cells, or fully differentiated cells from adipose tissue.

The methods and apparatus described herein can be used on site to prepare cellular compositions for administration to a patient (e.g., autologous administration). For example, the methods and apparatus described herein can be used to recover regenerative cells from a patient, referred to herein as a regenerative platform, that can be prepared for administration and then administered (e.g., injected or surgically implanted) back to the patient from which the cells were recovered. In some embodiments, the cells can be loaded into a delivery device such as a syringe, for injection into the recipient by, for example, subcutaneous, intravenous, intramuscular, or intraperitoneal techniques. For example, the regenerative cells can be injected into blood vessels for systemic or local delivery, into tissue (e.g., cardiac muscle or skeletal muscle), into the dermis (subcutaneous), into tissue space (e.g., pericardium or peritoneum), or other location. Injection of the regenerative platform can result in an area near the injection site being augmented, repaired, having reduced inflammation, reduced pain, and combinations thereof. In some embodiments, one or more additives are added to the cells before administration. For example, the cells can be mixed with other cells, biologically active compounds, biologically inert compounds, demineralized bone, a matrix or other resorbable scaffold, one or more growth factors, or other additive that can enhance the delivery, efficacy, tolerability, or function of the cell population.

The methods and apparatus also can be used to prepare cellular compositions for growth studies, gene expression studies, differentiation studies, or other research purposes. In addition, the methods and apparatus described herein can be used to recover regenerative cell populations (e.g., stem cells) such that the cells can be banked, for example, by cryopreserving the cells with an appropriate medium. For further reference, see U.S. Patent Application Publication No. 20100285588-A1.

In one embodiment, the methods described herein use a plurality of, i.e., two or more, acceleration and deceleration steps under centrifugal force to enhance the dissociation of the cells (e.g., regenerative cells such as stem or progenitor cells) from the extracellular matrix of the tissue. One acceleration and deceleration step under centrifugal force can be referred to as one round of centrifugation. In some embodiments, one or more of the following also can be used to enhance recovery of the cells: mechanical disruption, mechanical agitation, maintaining the temperature above room temperature (≥26° C.) and at or below 42° C. (e.g., about 37° C. to 40° C.), using enzymes to degrade the tissue, and separating different components of the tissue based on physical characteristics such as density, specific weight, and solubility. In some embodiments, the tissue is mechanically disrupted (e.g., by extrusion) before subjecting the tissue to two acceleration and deceleration steps under centrifugal force. In some embodiments, after mechanical disruption of the tissue, a first acceleration and deceleration step is performed under centrifugal force to separate the tissue into three general layers (i.e., an aqueous layer, a cell-enriched matrix containing the regenerative platform, and a lipid layer). The cell-enriched matrix can be removed, and subjected to a second acceleration and deceleration step under centrifugal force. In some embodiments, one or more enzymes (e.g., proteases) are added to the cell-enriched matrix before subjecting the cell-enriched matrix to the second acceleration and deceleration step. Such a process reduces the sample volume such that a smaller amount of enzymes is required to process the tissue. In some embodiments, a portion of the cell-enriched matrix is subjected to a second acceleration and deceleration step under centrifugal force, and the regenerative cells isolated from the cell pellet. The cell isolated from the portion of the cell-enriched matrix then can be combined with the cell-enriched matrix that has not been subjected to further centrifugation.

Using a reconfigurable centrifuge rotor that can be configured in an inverted position or in a swinging bucket configuration as described below is particularly useful in the methods described herein. When in the inverted configuration, centrifugal forces drive contents toward the outer, higher portion of a sample container, and at rest these contents return to the inner, lower portion of the sample container. Thus, by repeated cycles of acceleration and deceleration, an inverted rotor provides a means for agitation of a sample in a way, that at rest with gravitation and no acceleration forces, the contents of a container reside and move towards the center and axle of a centrifuge while with acceleration, the contents follow the centrifugal forces and go outward. When tissue is combined with a proteolytic enzyme solution as described herein, and placed in a container in the reconfigurable rotor in inverted position, repeated cycles of acceleration and deceleration facilitate the enzymatic dissociation of the tissue. When the reconfigurable rotor is configured in a typical swinging bucket rotor configuration, however, the contents of the sample container concentrate at the bottom and agitation therefore is reduced.

In order to significantly improve the recovery of regenerative cells and shorten the onsite application of the methods described herein in the operating theater, increasing the ambient temperature inside the centrifuge chamber during repeated cycles of acceleration and deceleration to 35 to 42° C. (e.g., 40° C.) increases the speed of enzymatic dissociation by several fold, compared to room temperature The methods and apparatus described herein increase the yield of cells recovered from the tissue sample relative to other methods in which a plurality of acceleration and deceleration steps under centrifugal force are not utilized. The increased yield of cells recovered using the methods and apparatus described herein are surprising in view of the findings by Kurita et al., Plast. Reconst. Surg., 121:1033-1041 (2008) in which centrifugation alone at constant speed is not sufficient to release increased numbers of viable stem cells from the extracellular matrix.

Figure 5:
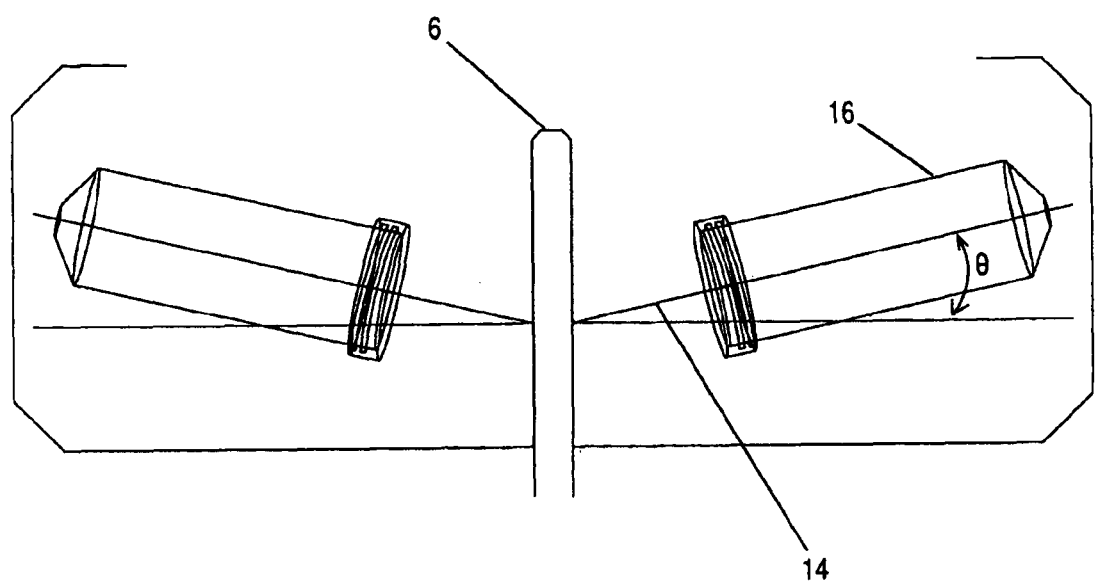
FIG. 5 is a side cross-sectional view of one embodiment of the apparatus of FIG. 1.

FIG. 1 is a perspective view of one embodiment of a centrifuge 1 having an inner chamber separated by a wall 2 (e.g., metallic wall) thereby creating an inner container 4. Typically, the diameter of the inner container 4 is 20-40 cm, depending on the size of the containers used for the cellular preparation. Within inner container 4 is an axle 6 driven by a motor 8 to rotate axle 6. The motor 8 typically is located below inner container 4. A controller 10 can turn the motor 8 on or off, and also can serve to regulate temperature inside inner container 4 as described below. Motor 8 through axle 6 turns rotor 12, which has two (as depicted) or more arms, each of which is capable of receiving and gripping container 16 in a firm link to the rotor arm 14. In one embodiment, rotor arm 14 can swing up and down based on the centrifugal forces exerted through motor 8 via axle 6, and depending on their speed, change their position from a vertical position to a fully 90 degree position when a certain g force (e.g., 20-30 g) is exceeded by the rotations per minute of the axle 6. In another embodiment, such as that depicted in FIG. 5, rotor arm 14 is set at a fixed angle θ (e.g., an angle ranging from 1 degree to less than 90 degrees). For example, the angle θ can be fixed at 12 degrees. In such an embodiment, container 16 can be attached to rotor arm 14 in an inverted orientation in which the top of container 16 containing a removable lid is oriented near the center by axle 6.

In some embodiments, the temperature of inner container 4 can be regulated such that the temperature of the inner container ranges, for example, from 26 to 42° C., 30 to 42° C., 35 to 42° C., 35 to 40° C., 37 to 40° C. or about 37° C. The temperature can be regulated by any known method, e.g., closed loop thermal feedback regulation. In one embodiment, electrical resistance wires (not shown in FIG. 1) can be wrapped around or embedded in the inner container 4 in order to warm up the inner container 4 through a connection to electricity, for example, via a cable. Such wires can be part of a heat pad or embedded in a flexible polymer. In order to keep the temperature constant, a temperature probe 18, which is operably linked to controller 10, can be used to sense the temperature in the inner container 4 and via controller 10, regulate the temperature within the inner container 4. Maintaining the temperature at 35 to 42° C. is particularly useful when one or more enzymes are used, as temperatures below this range can slow the dissociation process and temperatures above 42° C. can damage cells.

Controller 10 can be programmed to, for example, control the acceleration and deceleration steps, start and stop the motor 8, and regulate temperature. Controller 10 connects to a power source (e.g., through a plug or cable).

Controller 10 can be programmed to accelerate container 16 to achieve a g force of between 50×g and 4,000×g inclusive, maintain that g force for a short period of time, and decelerate the container 16 to 1×g within a short period of time. Repetitive cycles of the acceleration/deceleration steps can be applied over a time frame from 5 to 180 minutes (e.g., 5 to 120 minutes, 10 to 100 minutes, 20 to 60 minutes, 25 to 50 minutes, 30 to 45 minutes, about 30 minutes, or about 45 minutes). For example, each acceleration step can be performed for 5 to 20 seconds and each deceleration step can be performed for 3 to 20 seconds. In one embodiment, at least three cycles of acceleration to 200×g and deceleration to 1×g per minute can be performed for 30 minutes.

Figure 2:
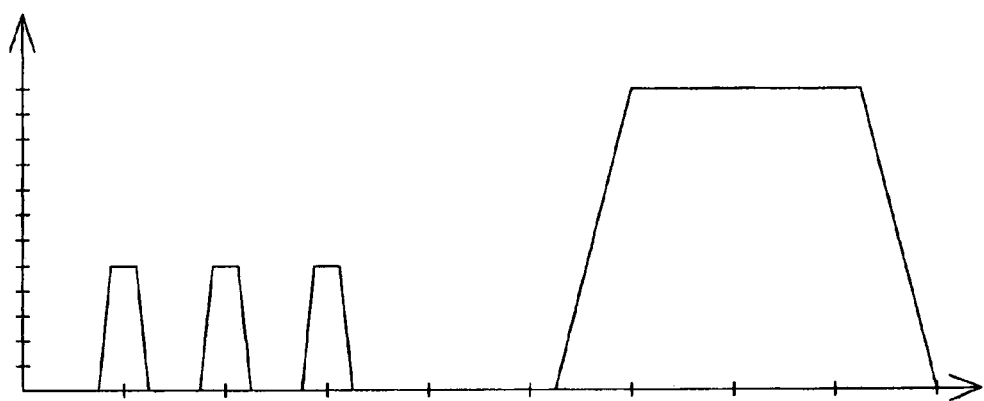
FIG. 2 is a graph of different time and energy cycles during the dissociation phase and combinations thereof.

FIG. 2 depicts examples of various time cycles that can be used to enhance the dissociation of cells from the extracellular matrix in the tissue sample contained in container 8 as shown in FIG. 1. Different patterns as depicted in FIG. 2 can be combined such as intermittent on and off and certain accelerations in which a certain g force is maintained over a longer period of time.

Figure 6:
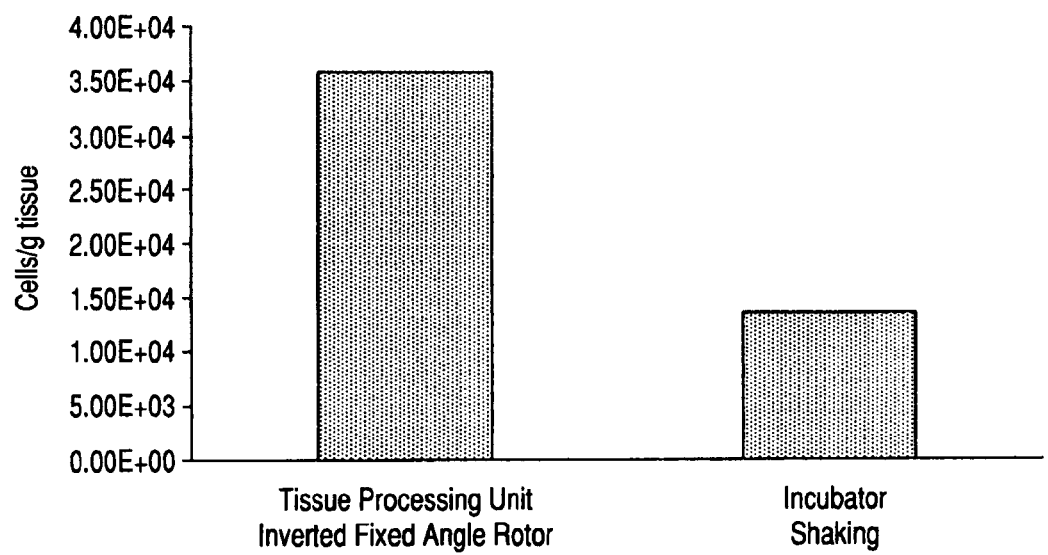
FIG. 6 is a bar graph of the number of adherent cells obtained after processing using an embodiment of the apparatus of FIG. 1 or after processing with a shaking incubator.

FIGS. 3A-3E depict containers, each of which is an exemplary embodiment of the container 16 shown in FIGS. 1 and 6. The containers in FIGS. 3A-3E are adapted for use in a centrifuge (e.g., a centrifuge depicted in FIG. 1 or FIG. 6). The containers have an insert that can aid in the dissociation of the cells from the extracellular matrix of the tissue when the containers are subjected to a plurality of acceleration and deceleration steps under centrifugal force, such as the centrifugal forces imparted by centrifuge 1 of FIG. 1. In each of FIGS. 3A-3E, container 300 includes an elongated cylindrical central portion 302, a closed end portion 304 integrally formed with the central portion, and an open end portion 306 integrally formed with the central portion defining an interior lumen 308. Closed end portion 304 can be substantially flat, rounded, hemispherical, conical, or any other appropriate shape. In some embodiments, the container 300 can have a length of approximately 10-12 cm. In some embodiments, the container 300 can have a volume of approximately 50-60 ml.

The open end portion 306 includes a mating portion 310 (e.g., a threaded portion) that is formed to accept a removable cap 312. The removable cap 312, when attached onto the mating portion 310, substantially encloses and seals the interior lumen 308 of the container 300. In some implementations, the cap 312 may be attached to the open end by threads, friction (e.g., a snap-on cap), by clamping, by magnetic attraction, by a vacuum seal, or by any other appropriate mechanism by which a vessel can be reversibly sealed.

Figure 3A:
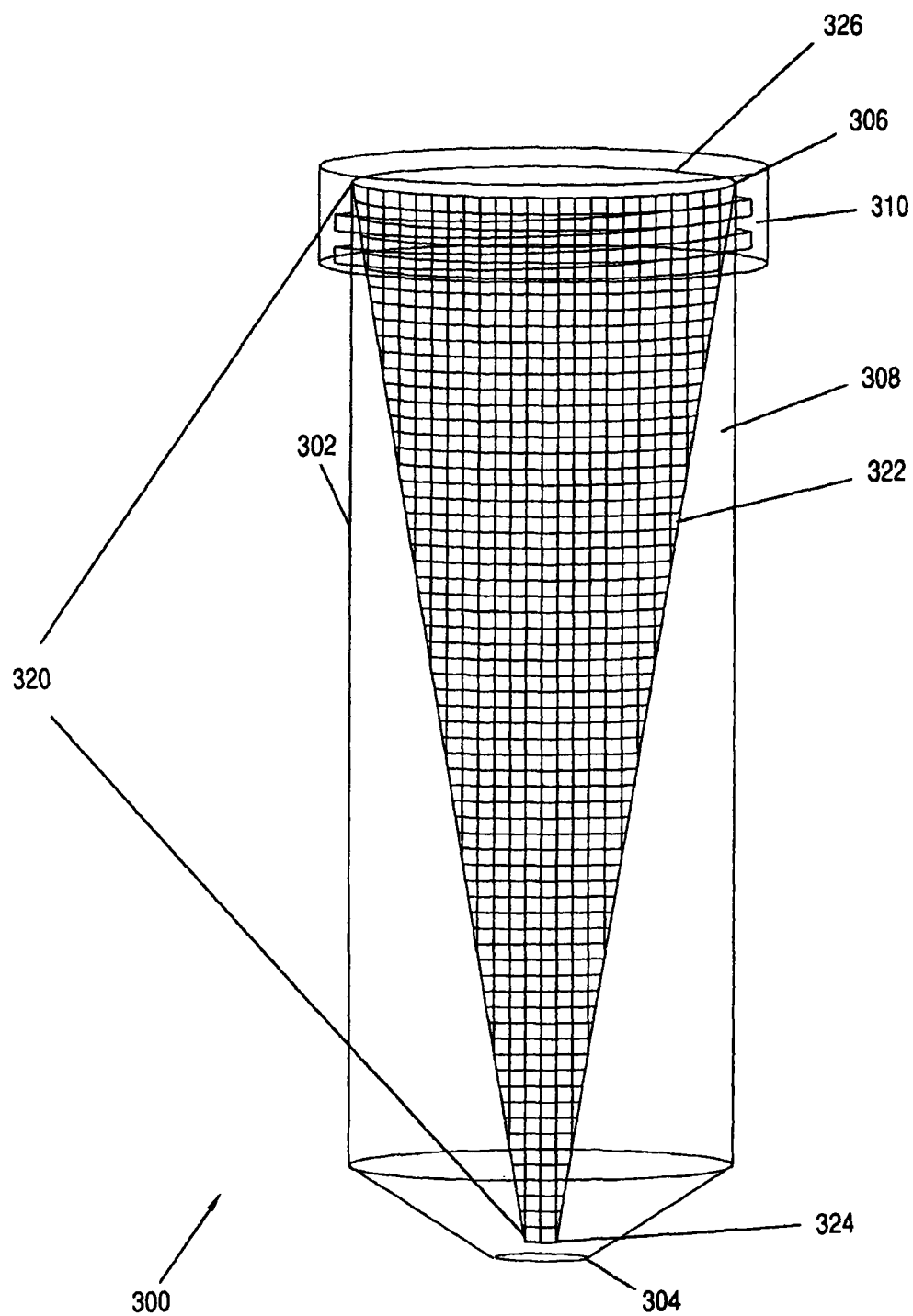
FIGS. 3A-3E are perspective views of different containers adapted for a centrifuge.

In FIG. 3A, container 300 includes an inverted substantially conical insert 320. The conical insert 320 is formed as an inverted hollow cone within the interior lumen 308. The inverted substantially conical insert 320 is substantially coaxial with the elongated cylindrical central portion 302, with a conical sidewall 322 that extends from a vertex 324 proximal to the enclosed end portion 304 to a base 326 proximal the open end portion 308.

The inverted substantially conical insert 320 is composed of a biocompatible material and is porous. Non-limiting examples of biocompatible materials include polyamides (e.g., Nylon); polyesters such as polycaprolactone; polystyrene; polypropylene; polyacrylates; polyvinyl compounds; polycarbonate; polyketones such as polyetheretherketone (PEEK); polytetrafluoroethylene (PTFE, Teflon); thermanox; nitrocellulose; poly(ortho esters); polyurethane; stainless steel; titanium; or titania (titanium dioxide). The pore size of the insert can range from 0.5 mm to 5 mm (e.g., 0.7 to 1.5 mm, 0.7 to 1.2 mm, 0.9 to 1.1 mm, 0.9 to 1.5 mm, 0.9 mm to 2.0 mm, 1 to 3 mm, 2 to 4 mm, 3 to 5 mm). In some embodiments, the inverted substantially conical sidewall 322 can be a screen, lattice, mesh, net, perforated sheet, or other suitable biocompatible porous substrate. In some embodiments, the inverted substantially conical insert can be a mesh with 1 mm pores.

The base 322 of the conical insert 230 has a diameter that is substantially the same as the diameter of the elongated cylindrical portion 302 at the open end 308. As such, the conical insert 320 is inserted into the interior volume 302 through the open end 308 until the base contacts the rim of the open end 306. The cap 312 is then removably affixed onto the open end 306, thereby substantially centering and affixing the conical insert 320 within the interior lumen 308. In some embodiments, the base 326 contains a flange that can be used to attach to the open end 308. Base 326 also can be secured directly to the bottom surface of the cap 312. Base 326 also can be secured directly to end 304.

In use, the inverted substantially conical insert 320 can be inserted into the container 300. The inverted substantially conical insert 320 can be filled with a tissue sample that includes a suspension of tissue pieces in an aqueous fluid, such that fluids and components of the tissue smaller than the pores are able to pass through the conical insert 320 to be captured by the cylindrical sidewall 304 and closed end 306.

In some embodiments, one or more proteases (e.g., one or more collagenases such as type I and/or type II collagenases, a neutral protease such as thermolysin, trypsin, or mixtures thereof) can be added to a container 300 to enhance the dissociation of the cells from the extracellular matrix of the tissue sample. For example, a type I collagenase, a type II collagenase, and a dispase can be used to enhance the dissociation of the cells from the extracellular matrix.

The cap 312, once applied, seals the interior lumen 308 and substantially affixes the conical insert 320 in position. The fluids and tissues are urged through the pores of the substantially conical insert 320 by the plurality of acceleration and deceleration steps. For example, the container 300, with a tissue sample loaded within the substantially conical insert 320, can be attached onto the rotor arm 14 of the centrifuge 1 of FIG. 1. The container 300 can then be accelerated and decelerated as discussed in the description of FIGS. 1 and 2. Under the repeated cycles of acceleration and deceleration, the tissue sample is urged in various directions through the pores of the insert. This process mechanically disrupts the tissue to enhance the release of the cells from the extracellular matrix.

Figure 3B:
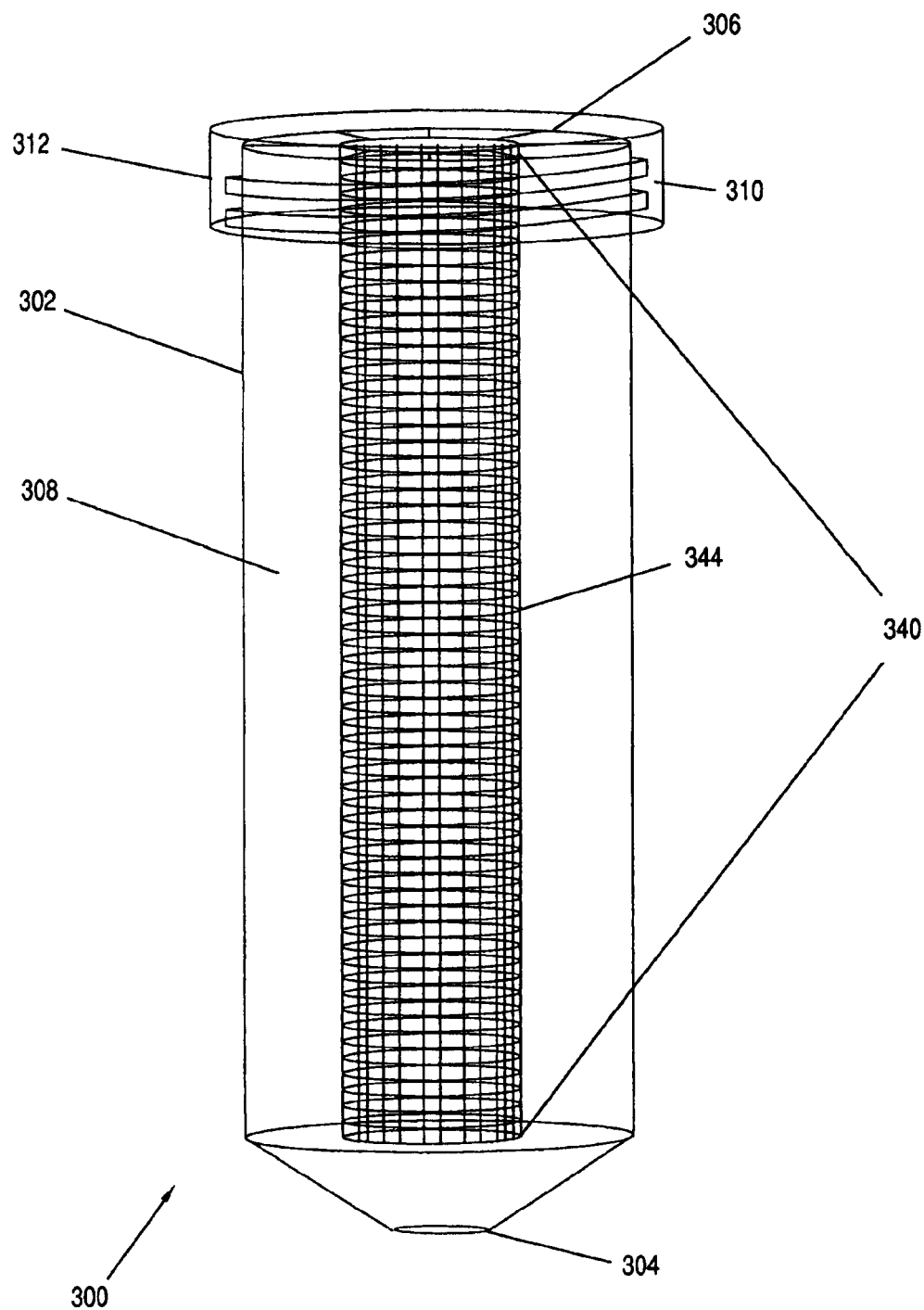

In FIG. 3B, container 300 include a substantially cylindrical insert 340. The substantially cylindrical insert 340 is formed as a cylinder within the interior lumen 308. The cylindrical insert 340 is substantially coaxial with the elongated cylindrical central portion 302, with a sidewall 344 that extends from closed end portion 304 to open end portion 306. The substantially cylindrical insert 340 is composed of a biocompatible material and is porous. Examples of suitable biocompatible materials and pore sizes are discussed above.

In use, the substantially cylindrical insert 340 can be inserted into the container 300. The substantially cylindrical insert 340 can be filled with a tissue sample containing a suspension of tissue pieces in an aqueous fluid such that fluids and components of the tissue smaller than the pores are able to pass through the cylindrical insert 340 to be captured by the elongated cylindrical central portion 302 and closed end 304. One or more enzymes also can be added to the container as discussed above. The cap 312, once applied, seals the interior volume 308 and substantially affixes the cylindrical insert 340 in position. The container 300 can then be accelerated and decelerated as discussed in the description of FIGS. 1 and 2. Under the repeated cycles of acceleration and deceleration, the tissue sample is urged in various directions through the pores of the insert. This process mechanically disrupts the tissue to enhance the release of the cells from the extracellular matrix.

Figure 3C:
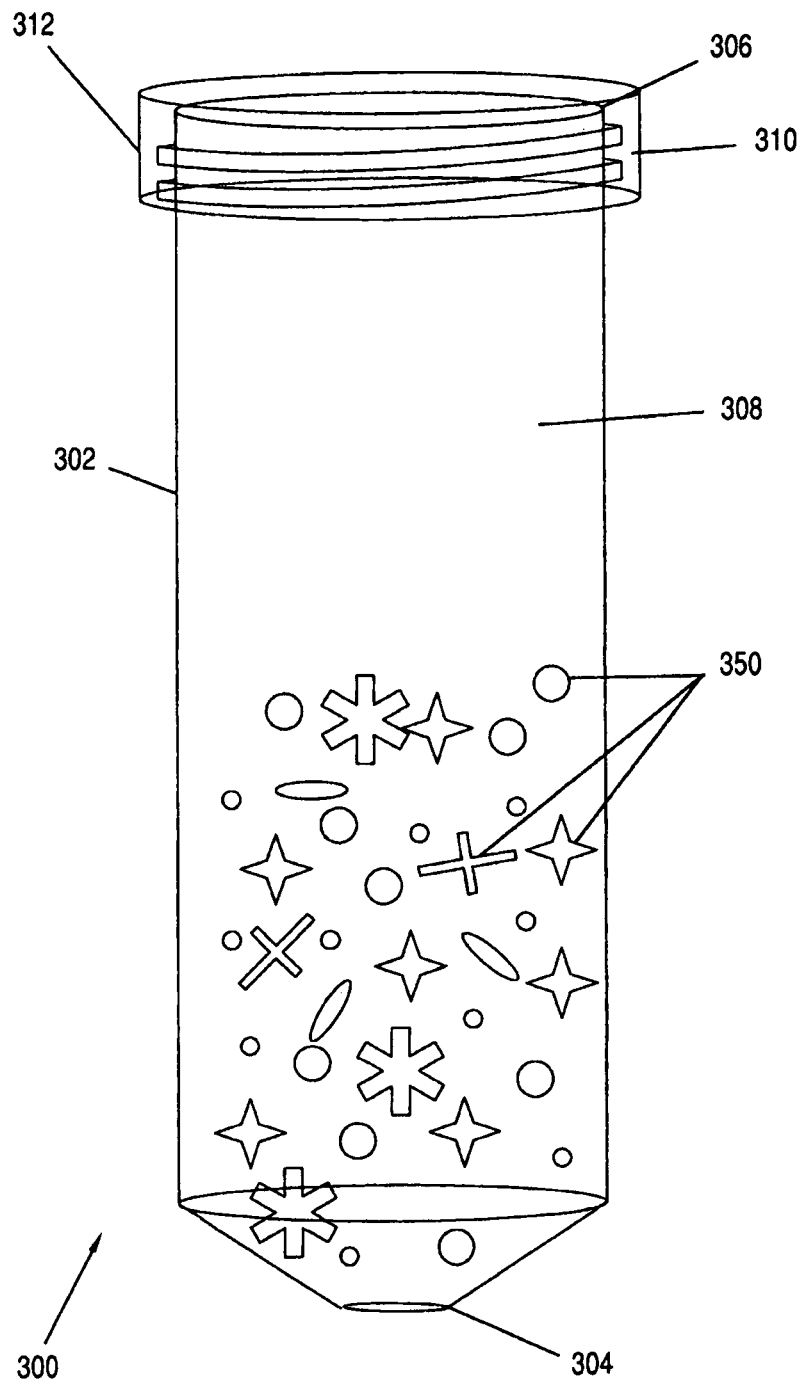
Figure 3D:
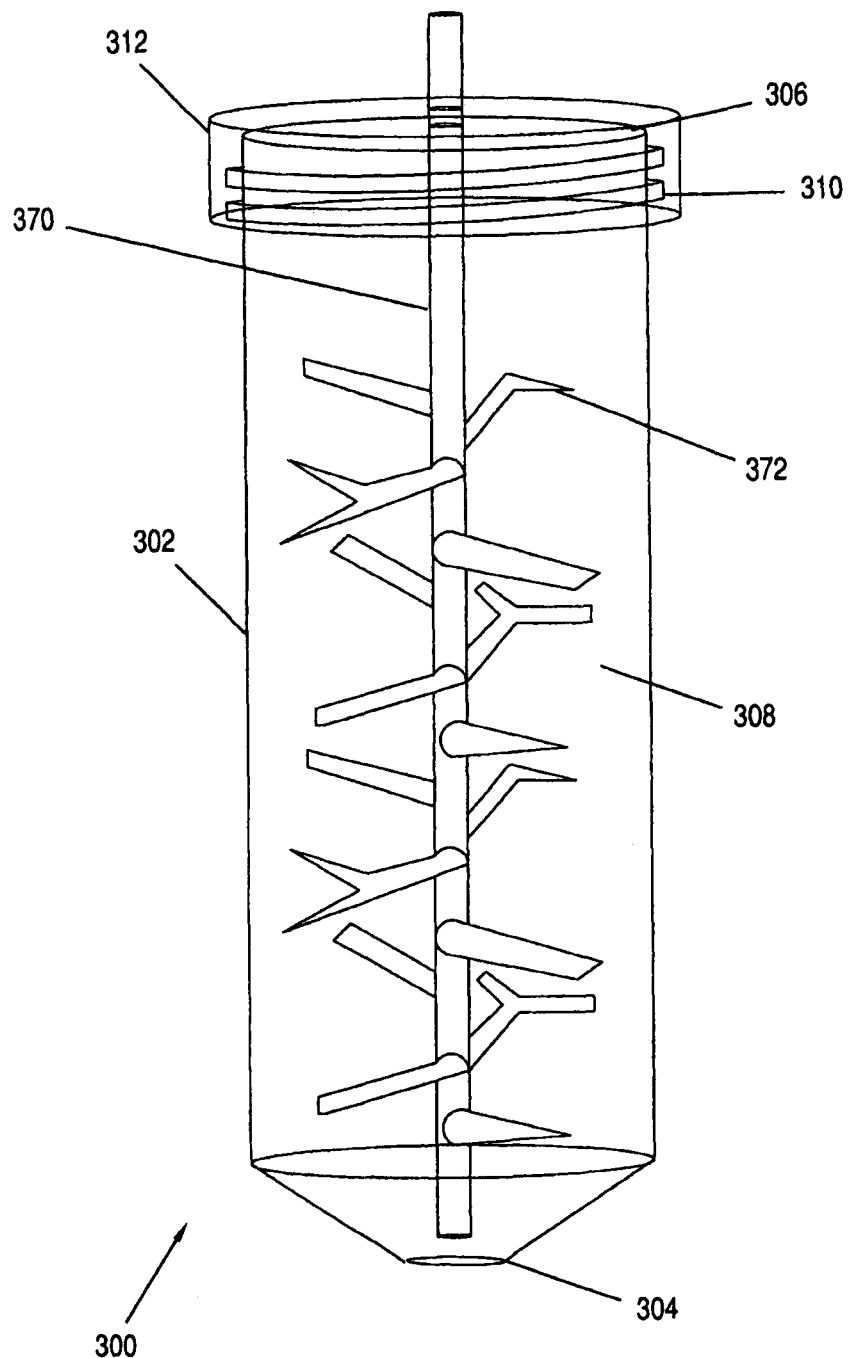
Figure 3E:
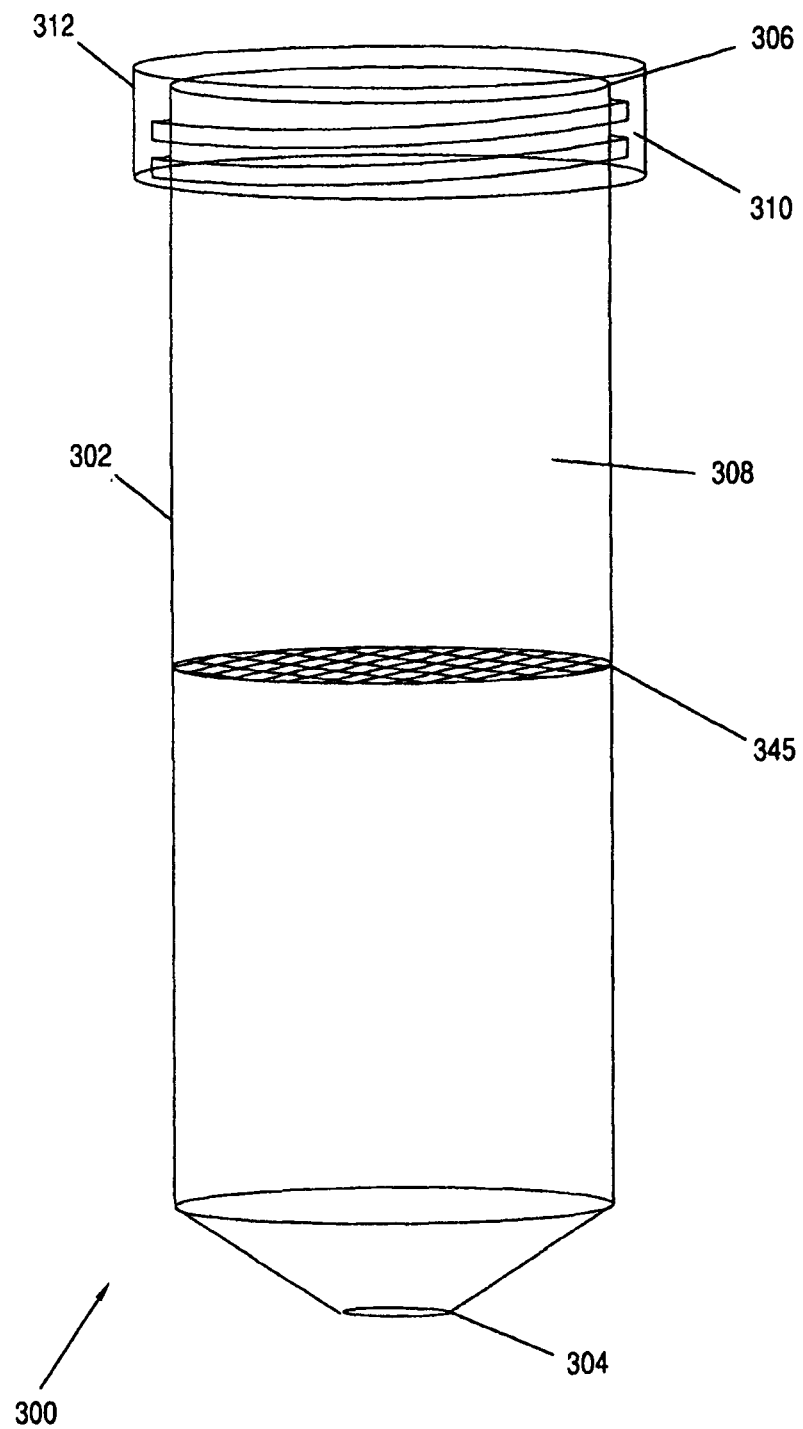

In FIG. 3E, the container 300 contains an insert 345 that bisects the container into upper and lower portions. The insert is composed of a biocompatible material and is porous. Examples of suitable biocompatible materials and pore sizes are discussed above. The insert can be held in place using, for example, a ring made out of rubber. In use, the tissue sample containing the suspension of tissue pieces in an aqueous fluid is loaded into the upper or lower portion of the container and subjected to the plurality of acceleration and deceleration steps to enhance the dissociation of the cells from the extracellular matrix. One or more enzymes also can be added with the tissue sample.

Referring now to FIG. 3C, a container 300 includes a plurality of particles 350 within the interior lumen 308. The pellets are at least 100 micrometers in diameter and are composed of one or more biocompatible materials or coated with one or more biocompatible materials. Non-limiting examples of biocompatible materials include polyamides (e.g., Nylon); polyesters such as polycaprolactone; polystyrene; polypropylene; polyacrylates; polyvinyl compounds; polycarbonate; polyketones such as PEEK; PTFE; thermanox; nitrocellulose; poly(ortho esters); polyurethane; stainless steel; titanium; titania (titanium dioxide); and glass. In some embodiments, the plurality of particles 350 can include particles of different specific gravities, shapes, or surface characteristics. In one embodiment, the plurality of particles 350 can include smooth polystyrene beads and particles with an iron coating.

In use, a tissue sample containing a suspension of tissue pieces in an aqueous fluid and the particles 350 are loaded into the container 300 and sealed with the cap 312. In some embodiments, one or more enzymes also are added to the container before sealing with the cap. The container is then loaded into the centrifuge 1 of FIG. 1 and is subjected to the plurality of acceleration and deceleration steps, which cause the particles 350 to be agitated and enhance the release of the cells from the extracellular matrix.

FIG. 3D shows another example of a container 300 containing an insert in which a shaft 370 is disposed vertically in the internal lumen 308 of the container. The shaft 370 includes a plurality of arms 372 disposed along a length of the shaft 370 and extending substantially radially from shaft 370 into the lumen 308. The arms 372 can be of different shapes and/or sizes as depicted in FIG. 3D.

In some embodiments, shaft 370 can be affixed to removable lid 312. Shaft 370 can be rotatably affixed to the container or removable container lid 312. For example, the shaft 370 can be rotatably affixed to, and extend through, the cap 312, such that the shaft 370 can be gripped and rotated from outside the container to agitate the tissue sample. In some embodiments, the shaft 370 can be rotatably affixed to the cap 312, and can be eccentrically weighted such that the shaft 370 can rotate under the force of gravity or centrifugation. In some embodiments, the shaft 370 can be rotatably affixed to the cap 312, and one or more of the arms 372 can include a magnet such that the shaft 370 can be magnetically coupled to a magnetic field external to the container. By rotating the magnetic field relative to the container, the shaft 370 can be urged to rotate within the interior lumen 308 to agitate the tissue sample. In some embodiments, shaft 370 can be moveable vertically within lumen 308 such that the arms 372 can pass up and down through the tissue sample. In some embodiments, the arms are sharpened blades.

In one embodiment, a tissue sample containing a suspension of tissue pieces in an aqueous fluid can be loaded into the container 300 and the cap 312 with the shaft 370 attached is affixed to seal the open end such that the arms 372 disposed along a length of shaft 370 are inserted into the interior lumen 308 and the tissue sample. One or more enzymes also can be added with the tissue sample. The container 300 can then be subjected to a plurality of acceleration and deceleration steps as discussed herein. The shaft 370 and associated arms 372 can enhance the dissociation of cells from the extracellular matrix of the tissue sample when subjected to the plurality of acceleration and deceleration steps.

Figure 4:
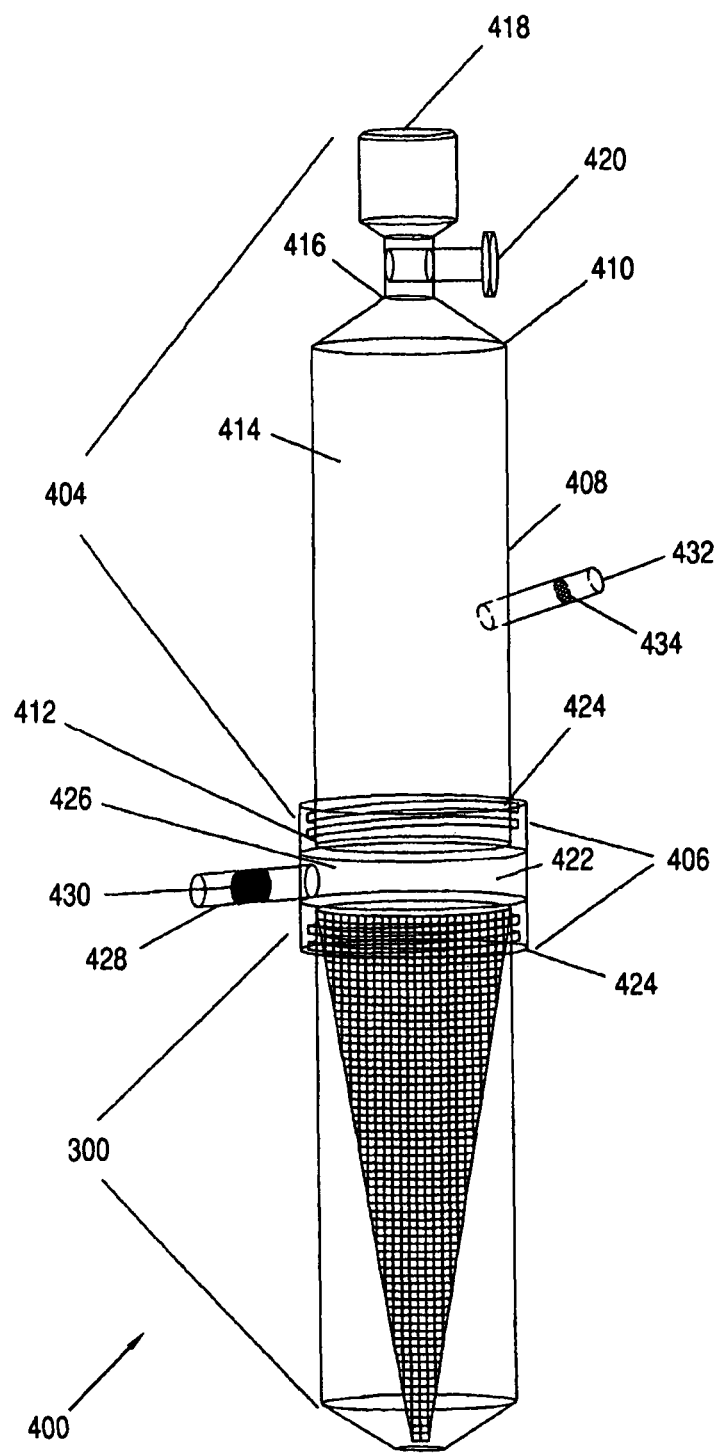
FIG. 4 is a perspective view of a container assembly according to one embodiment described herein.

FIG. 4 shows an example of a container assembly 400 of a first container 300, second container 404, and a coupling device 406. In the embodiment depicted in FIG. 4, the assembly 400 includes the container 300 of FIG. 3A and a container 404. In some embodiments, the container 300 can be any of the containers depicted in FIGS. 3B-3E. The container 404 includes an elongated cylindrical central portion 408; a first end portion 410 integrally formed with central portion 408; and a second open end portion 412 integrally formed with central portion 408, defining an internal lumen 414.

In some embodiments, a port 432 can extend radially outward from the elongated cylindrical portion 408 and provide a fluidic passage that extends from the interior lumen 414 to the outside. Such a port also can include a porous insert 434. In some embodiments, the porous insert can have pores of approximately 0.2 microns, which can allow air to pass but prevent contaminants from entering the interior lumen 414.

The first end portion 410 narrows down to a narrow opening 416, and contains a collection portion 418 protruding from end portion 410 at the narrow opening 416. The collection portion 418 is capable of receiving and storing a fluid and includes a removable plug 420 to seal the first end portion 410 from the collection portion 418. The removable plug 420 allows fluid to flow from the end portion 410 into the collection portion 418 upon centrifugal force, pressure, dissociation with an enzyme, or physical removal. In some embodiments, the removable plug is a valve that can be activated to provide access to the collection portion. In some embodiments, the collection portion is detachable from the first end portion.

In some embodiments, the collection portion 418 comprises an aqueous fluid that is separated from the interior lumen 414 via removable plug 420. For example, collection portion 418 can include sterile saline, buffer, cell culture medium, one or more biologically active compounds, one or more biologically inert compounds, demineralized bone, a matrix or other resorbable scaffold, one or more growth factors, or other additive that can enhance the delivery, efficacy, tolerability, or function of the cell population.

The second end portion can contain a mating portion (e.g., a threaded portion) such that a cap can be attached to substantially seal the container.

Container 404 can be removably connected to container 300 using coupling device 406, which includes a tubular central portion 422 with first and second open ends 424 and a porous insert 426 extending horizontally across coupling device 406. Each open end 424 includes a mating portion (e.g., a threaded portion). The porous insert has a pore size of 40 to 500 micrometers and extends horizontally across coupling device 406 such that porous insert 426 substantially separates the interior volume 308 from the interior volume 414. In some embodiments, two or more porous inserts can be disposed on top of one another. For example, a porous insert with relatively larger pore sizes can be disposed more closely to the container 300, while the porous inserts with relatively smaller pore sizes can be disposed more closely to the container 404. As such, fluids and particles flowing from the container 300 to the container 404 can pass through progressively smaller pores as they pass through the porous insert 426.

Coupling device 406 further can include a port 428 extending radially outward from the tubular central portion 422 to provide a fluidic passage from the interior of the coupling device. The port can include a porous insert 430 with a pore size of 0.2 to 500 micrometers. In some embodiments, porous insert 430 can have pores of approximately 0.2 microns, which can allow air to enter into the interior of the coupling device 406, but filter out bacteria and particulate matter than could contaminate the containers 300, 404 or the tissue sample.

One mating portion of the coupling device can be attached to the mating portion of container 300 and the other mating portion of the coupling device can be attached to the mating portion of container 404. In embodiments in which the open end portions of containers 300 and 404 are threaded, coupling device 406 is threaded on each end to allow the containers 300 and 404 to be threaded into coupling device 406 by their threaded portions. In some embodiments, containers 300 and 404 are pre-assembled such that an interior space defined by the first container and the second container is at least partially under vacuum.

In use, the container 300 can be uncoupled from coupling device 406 and loaded with a tissue sample, buffer (e.g., lactated Ringer's), and optional enzyme. A cap (e.g., the cap 312) is applied to removably seal the container 300. The container 300 and the tissue sample within can be processed in the centrifuge 1 as discussed above. After subjecting the sample contained within container 300 to the plurality of acceleration and deceleration steps as discussed above, the cap 312 can be removed and coupling device 406 can be attached to container 300 and container 404. The liquid components within container 300 can be forced into container 404 by inverting the container assembly and applying negative pressure to port 432. For example, a small piece of tubing can be attached to port 432 and suction applied using a syringe (e.g., with a Luer connection) to create a negative pressure in container 404 such that fluid and cells within the fluid in container 300 are forced through the porous insert 426 and into the interior lumen 414 of container 404.

After transfer to container 404, container 300 can be detached from the coupling device and the coupling device can be detached from container 404. A cap can be removably attached to the mating portion 420 to substantially seal the container 404. Cells dissociated from the extracellular matrix then can be recovered from other cellular components by centrifuging the container at 400 to 4000×g. In some embodiments, the cells are collected in the collection portion 418 of container 404.

In some embodiments, the centrifugation at 400 to 4,000×g can be performed as a second program carried out using centrifuge 1. For example, the second program can be programmed into controller 10. The container 404 can be inserted into the rotor arm 14 in a fixed angle embodiment in which the cap is oriented toward the center of the rotor and the collection portion 418 is oriented away. Container 404 can be centrifuged for about 5 to 10 minutes with a g force of about 400×g to 4,000×g (e.g., 400 to 1,000×g). Centrifugation at such g forces allows for separation and collection of cells at the collection portion 418.

In some embodiments, one or more cell separation reagents, including magnetic beads or antibodies or antigen binding fragments thereof can be used in conjunction with the methods and apparatus described herein. For example, antibodies having binding affinity for a particular cell type can be used to recover cells of that type from cells collected within the collection portion. In some embodiments, such cell separation reagents are included within container 300. In some embodiments, such cell separation reagents are included within container 404.

In some embodiments, a tissue sample is subjected to one acceleration and deceleration step under centrifugal force to prepare a cell-enriched matrix, which is then subjected to one or more acceleration and deceleration steps. For example, a tissue sample housed in a tissue collection container can be centrifuged to produce a cell-enriched matrix that includes a regenerative platform therein. Regenerative platform refers to regenerative cells such as stem cells, progenitor cells, and/or hematopoietic cells within the concentrate. An example of such a cell preparation is given in US 2010/0124563 A1. The tissue sample may have a regenerative platform throughout the tissue sample; however, centrifugation causes the tissue sample to form a cell-enriched matrix having a concentrated amount of the regenerative platform therein. For example, upon centrifugation of a tissue sample within a tissue collection container, three general layers form (e.g., an aqueous layer, a cell-enriched matrix having the regenerative platform, and a lipid layer). The cell-enriched matrix is generally located between the lipid layer and the aqueous layer. After the extraction of the aqueous layer, the cell-enriched matrix can be easily extracted from the tissue collection container (e.g., using a closed system) for further use of the cell-enriched matrix.

An automated tissue processing unit can be used to centrifuge the tissue sample. For example, an automated tissue processing unit having a removable rotating apparatus therein, where the removable rotating apparatus is configured to rotate within the automated tissue processing unit, can be used to generate the centrifugal force. The automated tissue processing unit may include a temperature control device for controlling the temperature within the unit.

Figure 8:
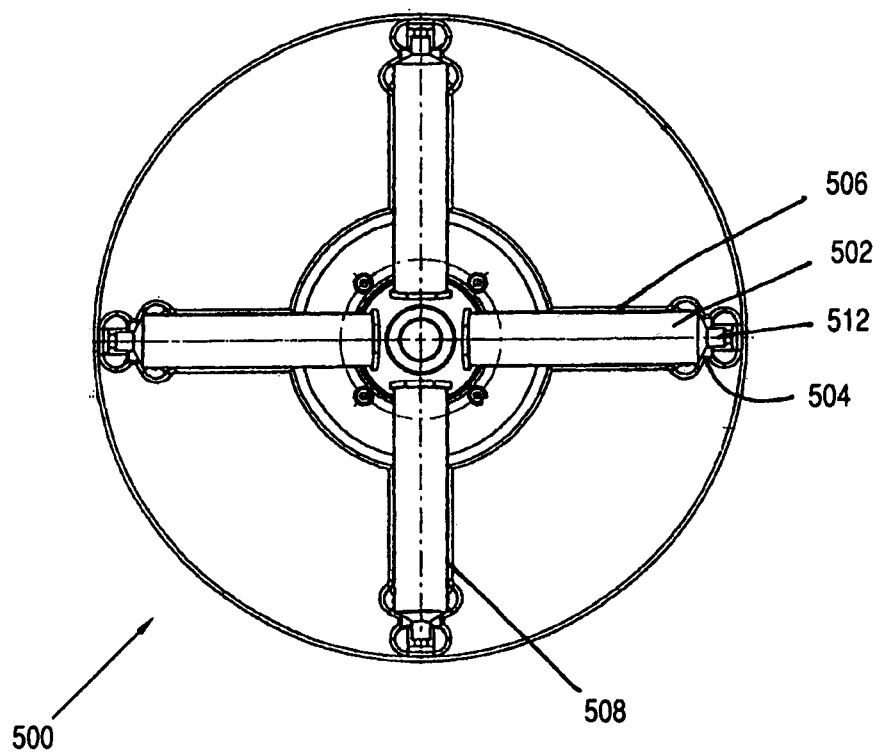
FIG. 8 is a top view of a removable rotating apparatus that may be inserted into an automated tissue processing unit.

FIG. 8 is a top view of a removable rotating apparatus 500 that may be inserted into an automated tissue processing unit (not shown). A tissue collection container 502 may be detachably inserted into the removable rotating apparatus 500 and held in place by a locking mechanism 504 (e.g., snappable locking mechanism). Here, the tissue collection container 502 snaps into the cavity 506. In one non-limiting embodiment, the tissue collection container 502 is customizable to snappably fit within the cavity 506 and held in place by the snappable locking mechanism 504. The tissue collection container 502 is oriented so that the opening 512 of the tissue collection container 502 is farthest from the center. The formation of a cell-enriched matrix may form near the opening 512, and the cell-enriched matrix may be easily extracted from the tissue collection container 502 through the opening without additional contamination to the cell-enriched matrix.

The removable rotating apparatus 500 may have at least two cavities (shown here as 506, 508) or may have up to about eight cavities in another non-limiting embodiment. Each cavity 506, 508 may be in a horizontal orientation and may have a detachable mechanism for inserting a tissue collection container 502 within the cavity 506, 508. The detachable mechanism may be, but is not limited to a snapping mechanism, Velcro, and the like, and combinations thereof. In another non-limiting embodiment, the removable rotating apparatus 500 may have or include autoclavable materials, such that the removable rotating apparatus 500 is configured to be autoclavable.

Figure 9:
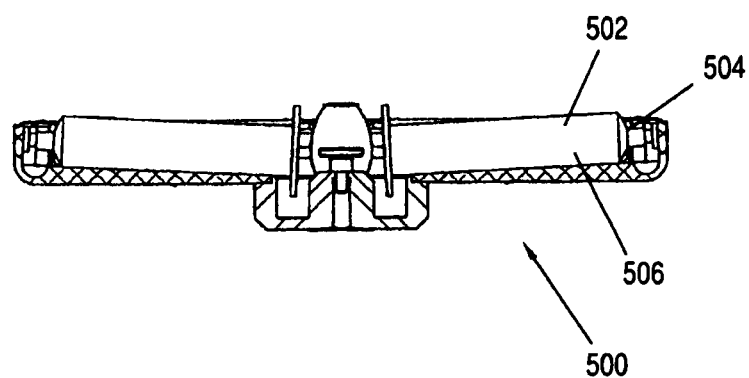
FIG. 9 is a side view of a removable rotating apparatus that may be inserted into an automated tissue processing unit.

FIG. 9 is a side view of a removable rotating apparatus 500 that may be inserted into an automated tissue processing unit (not shown). The tissue collection container 502 is shown within the cavity 506 and held in place by the locking mechanism 504. It will be appreciated that the removable rotating apparatus illustrated in FIGS. 8-9 is not to scale or proportion and that certain features of it may be exaggerated or distorted for illustrative purposes.

The automated tissue processing unit may also have a mechanism for identifying a particular removable rotating apparatus by at least one pre-determined specification of the removable rotating apparatus. In one embodiment, the removable rotating apparatus may have an attached RFID tag. The RFID tag may be scanned upon placement of the removable rotating apparatus into the automated tissue processing unit for identification by the automated tissue processing unit.

In another embodiment, a specification of the removable rotating apparatus within the automated tissue processing unit may be measured and recorded, such as, but not limited to, the power demand associated with acceleration, weight, wind resistance, and combinations thereof. The measured specification may be stored as part of a software program and/or software package of the automated tissue processing unit that enables the automated tissue processing unit to identify the removable rotating apparatus by such specification data.

The tissue sample may be housed in a first tissue collection container adapted for the automated tissue processing unit. The tissue sample may have or include a suspension of tissue pieces in an aqueous fluid. In one non-limiting embodiment, the tissue sample may be extruded prior to placement of the tissue sample into the first tissue collection container. The tissue sample may be extruded between one and twenty times, or alternatively from about two times to about ten times through an orifice ranging in diameter from about 1 mm independently to about 4 mm, or alternatively from about 1.5 mm independently to about 3 mm. Extruding the tissue sample before subjecting it to a round of acceleration produces a cell-enriched matrix that has a higher concentration of the regenerative platform compared to an otherwise identical method absent the extrusion of the tissue sample. As used herein with respect to a range, "independently" means that any lower threshold may be used together with any upper threshold to give a suitable alternative range.

The tissue sample may be subjected to centrifugation to achieve a g force ranging from about 200×g independently to about 2000×g, or alternatively at least 400×g using the automated tissue processing unit. The centrifugation may occur for a time period ranging from about 3 minutes independently to about 60 minutes, or at least about 5 minutes. After the centrifugation, a cell-enriched matrix may form.

The cell-enriched matrix can be transferred from the first tissue collection container into a second collection container by a closed system method. Such a closed system method may include, but is not limited to, a mechanism such as a leur connector between the first collection container and the second collection container, a spike port, a needle, or combinations thereof. The closed system method of transfer prevents the cell-enriched matrix that includes a regenerative platform from being contaminated by any additional pathogens external to the tissue sample and/or the tissue collection containers, such as but not limited to bacteria, viruses, and the like from entering into the tissue collection containers or the cell-enriched matrix. The closed system decreases the necessity for additional steps to be performed on the cell-enriched matrix prior to the administration of the tissue sample back into a subject as described above. As used herein, the numeral notation of 'first tissue sample container' and 'second tissue sample container' denotes the usage order of the containers. The containers may be the same types of containers or different types of containers, e.g., a vial or centrifuge tube.

The second tissue collection container may then be subjected to at least one more acceleration and deceleration steps, as described above. Each round of acceleration and deceleration may occur until at a rate of at least about 10×g is obtained. Alternatively, the rate of acceleration and deceleration may occur at a rate ranging from about 10×g to independently about 400×g, or from about 20×g independently to about 40×g in another non-limiting embodiment. In one non-limiting embodiment, the number of rounds per minute of acceleration and deceleration may range from about 1 round per minute to about one round per five minutes, or alternatively at least about three rounds per minute. In another non-limiting embodiment, the cell-enriched matrix may be disaggregated after a number of rounds of acceleration and deceleration, or alternatively at least two rounds of acceleration and deceleration.

In some embodiments, one or more proteases (e.g., one or more collagenases such as type I and/or type II collagenases, a neutral protease such as thermolysin, trypsin, or mixtures thereof) can be added to the second tissue container. One or more of the proteases may be recombinantly produced. For example, one or more collagenases can be added to the second tissue collection container in an amount ranging from about 0.5 Wunsch units collagenase per ml independently to about 4.0 Wunsch units collagenase per ml, or alternatively from about 1.0 Wunsch units collagenase per ml independently to about 3.0 Wunsch units collagenase per ml. The intermittent rounds of acceleration followed by deceleration in the presence of a protease may disaggregate the regenerative platform of the cell-enriched matrix.

After the acceleration and deceleration steps, the cell-enriched matrix may be filtered and washed to obtain a regenerative platform that may be administered back into a subject by implantation or injection as described above. For example, the cell-enriched matrix can be filtered to obtain an injectable regenerative platform, in which a few or no additional steps must be performed for the regenerative platform to be injected into a subject.

The invention will be further described with respect to the following Example which is not meant to limit the invention, but rather to further illustrate the various embodiments.

EXAMPLES

Example 1

Fresh canine omental adipose tissue was obtained from tissue discarded after spay surgery. Tissue was minced with sterile scissors and then equally divided (approximately 2 g/tube) into 50 mL sterile centrifuge tubes. Sterile lactated Ringer's containing a blend of bacterial collagenases I and II together with dispase was added and the tubes were then randomly assigned to incubation in a shaking incubator (60 rpm) or a heated tissue processing apparatus in a fixed rotor (TPA, 3 cycles per min of 1×g to 200×g to 1×g). Temperature was maintained between 37-40° C. and incubation/processing was conducted for 30 min.

After processing, the dissociated tissue slurry was passed through a 100 μm filter and the cell fraction was recovered from the filtrate by centrifugation at 400×g for 10 min in the TPA. Cell fractions were plated in 25 cm$^2$ tissue culture flasks and grown for two days at 37° C. in DMEM/20% (v/v) fetal bovine serum (FBS) containing antibiotic and antimycotic. After culturing for two days, adherent cells were counted using a hemacytometer. FIG. 6 is a bar graph of the number of adherent cells obtained after processing using the TPA and using the shaking incubator. Processing the tissue with the TPA resulted in a 2.6 fold higher than when dissociatiion was performed in a shaking incubator.

Example 2

Fresh human adipose lipoaspirate was obtained with patient informed consent from a patient undergoing elective lipoplasty. Tissue was drained using a sterile stainless steel strainer and then equally divided (approximately 10 g/tube) into 50 ml sterile centrifuge tubes with (see, FIGS. 3A, 3D, and 3E) or without inserts fabricated from nylon mesh with 1 mm pore size. Sterile lactated Ringer's containing a blend of bacterial collagenases I and II together with dispase was added and the tubes then were randomly assigned to incubation in a shaking incubator (60 rpm) or a heated TPA in a swinging bucket rotor (3 cycles per min of 1×g to 200×g to 1×g). Temperature was maintained between 37-40° C. and incubation/processing was conducted for 30 min.

Figure 7:
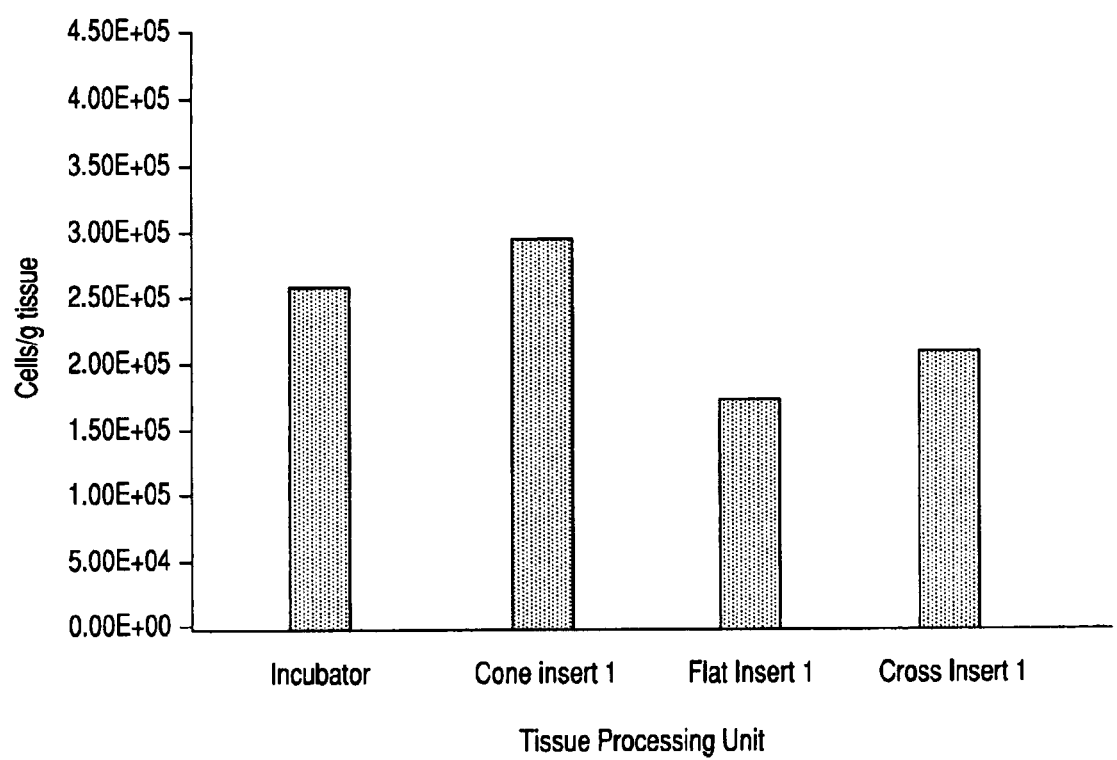
FIG. 7 is a bar graph of the number of adherent cells obtained after processing using an embodiment of the apparatus of FIG. 1 and containers of FIG. 3A, 3D, or 3E, or after processing using a shaking incubator.

After processing, the dissociated tissue slurry was passed through a 100 μm filter and the cell fraction was recovered from the filtrate by centrifugation at 400×g for 10 min in the TPA. Cell fractions were plated in 25 cm² tissue culture flasks and grown for two days in DMEM/20% (v/v) FBS containing antibiotic and antimycotic. After culturing for two days, adherent cells were counted using a hemacytometer. FIG. 7 is a bar graph of the number of adherent cells obtained after processing using the TPA and three different inserts, or after processing using the shaking incubator. Results indicate that cell yield obtained by processing in the TPA and using the cone insert (e.g., FIG. 3A) is similar to cell yield obtained by processing in the incubator.

Example 3

A lipoaspirate sample was obtained from a human patient undergoing elective lipoplasty. Lipoaspirate was transferred to a plurality of tissue collection containers having a 20 cc volume. Lipoaspirate contents of each of the tissue collection containers were extruded five times through a micro-emulsifying needle. The extruded lipoaspirate from each of the tissue collection containers was then transferred to a separate tissue collection container. The tissue collection containers were then placed into the cavities of a removable rotating apparatus within an automated tissue processing unit. The removable rotating apparatus allowed the tissue collection containers to maintain a horizontal position, while the automated tissue processing unit applied acceleration and centrifugal force to the contents of the tissue collection containers. The centrifugal force was applied for 30 minutes at a rate of about 400×g, about 700×g, about 1200×g, or about 2000×g for 30 minutes. The contents of two tissue collection containers were used for each rate of centrifugal force.

After the centrifugation, a cell-enriched matrix having a regenerative platform was separated from the remainder of the tissue sample within each tissue sample collection container. The volume of the layer of oil, a lipoaspirate fraction, and an aqueous fraction was removed and measured for each sample. The lipoaspirate layer was placed into a separate 50 cc conical centrifuge tube.

As a control sample, approximately 5 g of unprocessed, i.e., neither extruded nor centrifuged, lipoaspirate was transferred to each of 2 tissue collection containers. The containers were weighed and the weight of the transferred lipoaspirate was recorded. Ringer's lactate that includes a collagenase enzyme and a dispase enzyme was added to the unprocessed lipoaspirate in an amount of 5 mL to each tissue collection container. The tissue collection containers were then placed into a shaking incubator at about 37° C., and about 60 rpm for about 30 min to disaggregate the unprocessed lipoaspirate. The disaggregated tissue sample was then passed through a 100 μm steriflip filter. The filtered tissue was then centrifuged at a rate of about 600×g for about 10 minutes to recover regenerative cells. The recovered cells were placed in culture in minimum essential medium (MEM) with 20% (v/v) fetal bovine serum for 24 hours. The adherent cells were counted by a hemacytometer.

Figure 10:
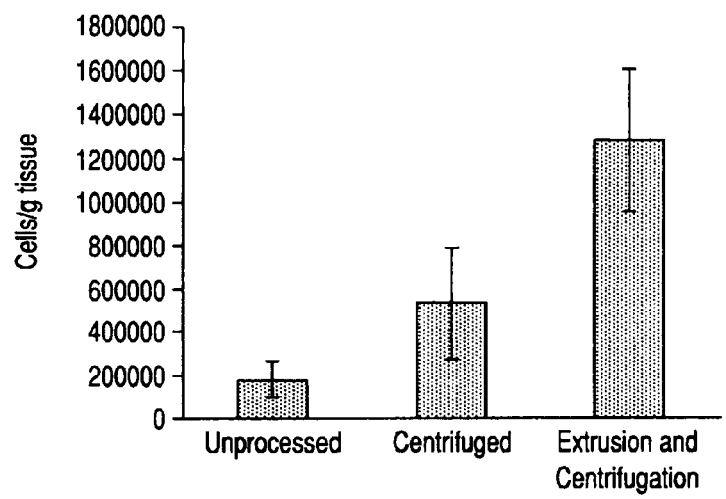
FIG. 10 is a graph of the number of adherent cells/g tissue obtained from adipose tissue that was treated as follows: not centrifuged, centrifuged, or extruded then centrifuged.
Figure 11:
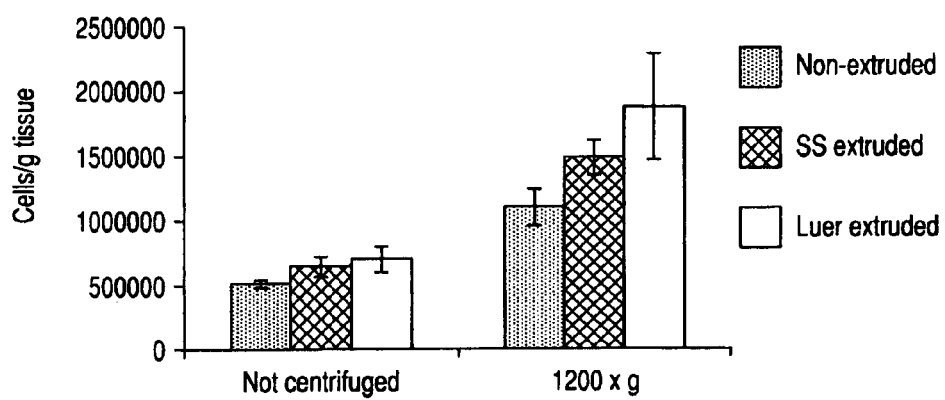
FIG. 11 is a graph of the number of cells/g tissue obtained from adipose tissue that was not extruded, extruded through an emulsion needle (SS extruded), or Luer extruded, and then either not centrifuged or centrifuged at 1200×g. For extrusion the tissue was passed 5× across the extrusion device using syringes

As illustrated in FIG. 10, extruding the tissue sample prior to centrifugation yields a greater number of cells per gram of tissue. FIG. 11 illustrates that centrifugation at 1200×g has an additive effect in terms of increasing the cell concentration within the cell-enriched matrix regardless of whether the tissue was extruded prior to centrifugation.

Figure 12:
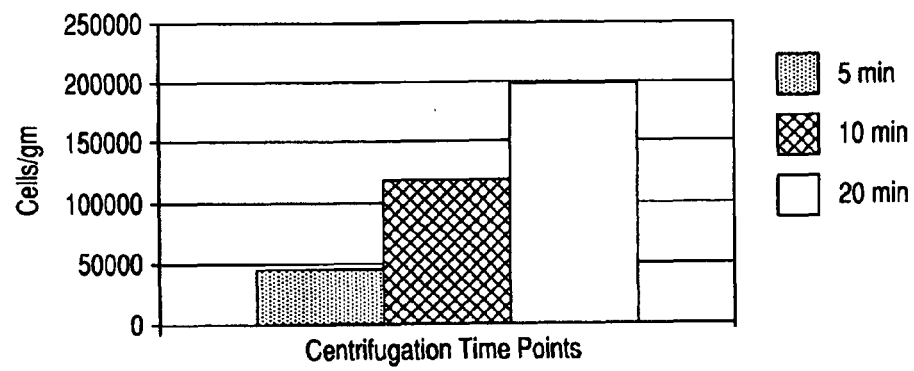
FIG. 12 is a graph of the number of adherent cells/g tissue obtained from adipose tissue after 5, 10, or 20 minutes of centrifugation.
Figure 13:
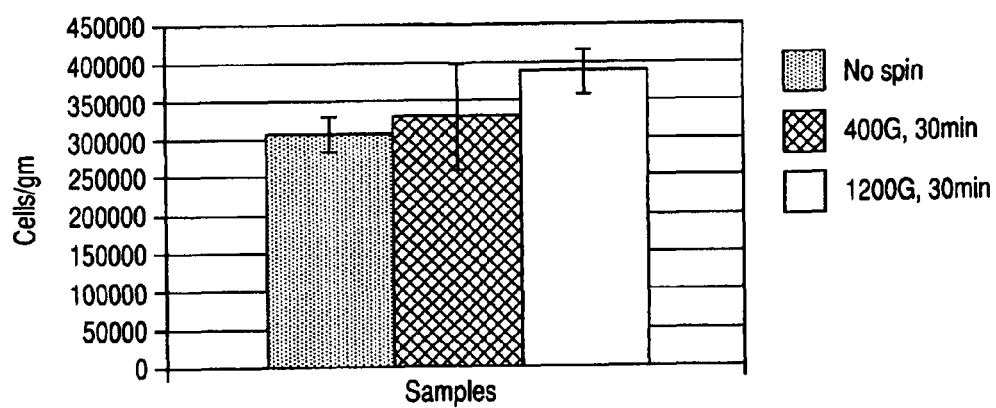
FIG. 13 is a graph of the number of adherent cells/g tissue obtained from adipose tissue after no centrifugation, centrifugation at 400×g for 30 minutes, or 1200×g for 30 minutes.
Figure 14:
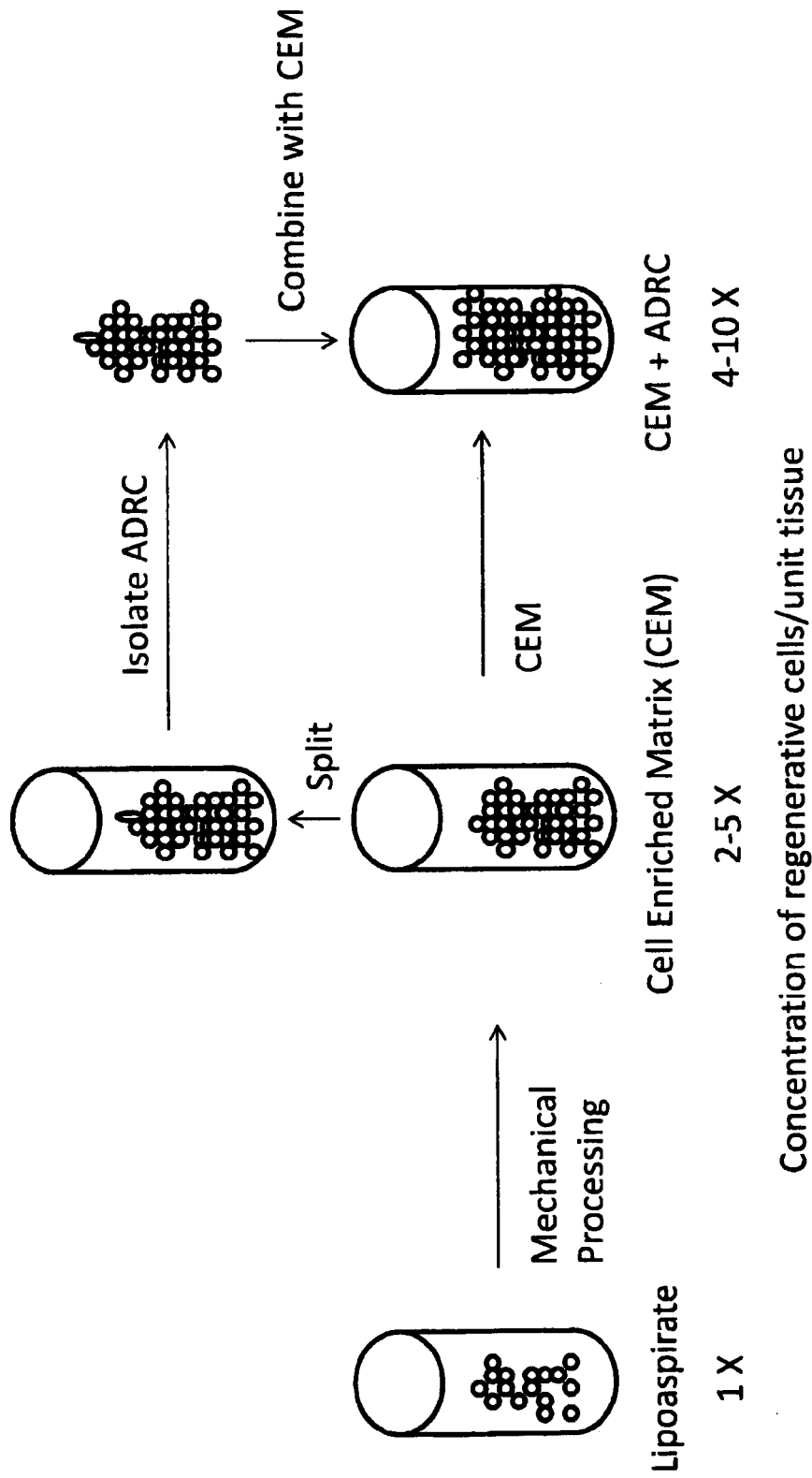
FIG. 14 is a schematic of a method to increase the concentration of adipose derived regenerative cells (ADRC) in a tissue preparation for grafting. Tissue is first processed to concentrate ADRC in the cell-enriched matrix (CEM). One-half of the CEM is processed to yield isolated ADRC, which are then combined with the remaining CEM to further increase the concentration of ADRC in the graft.
Figure 15:
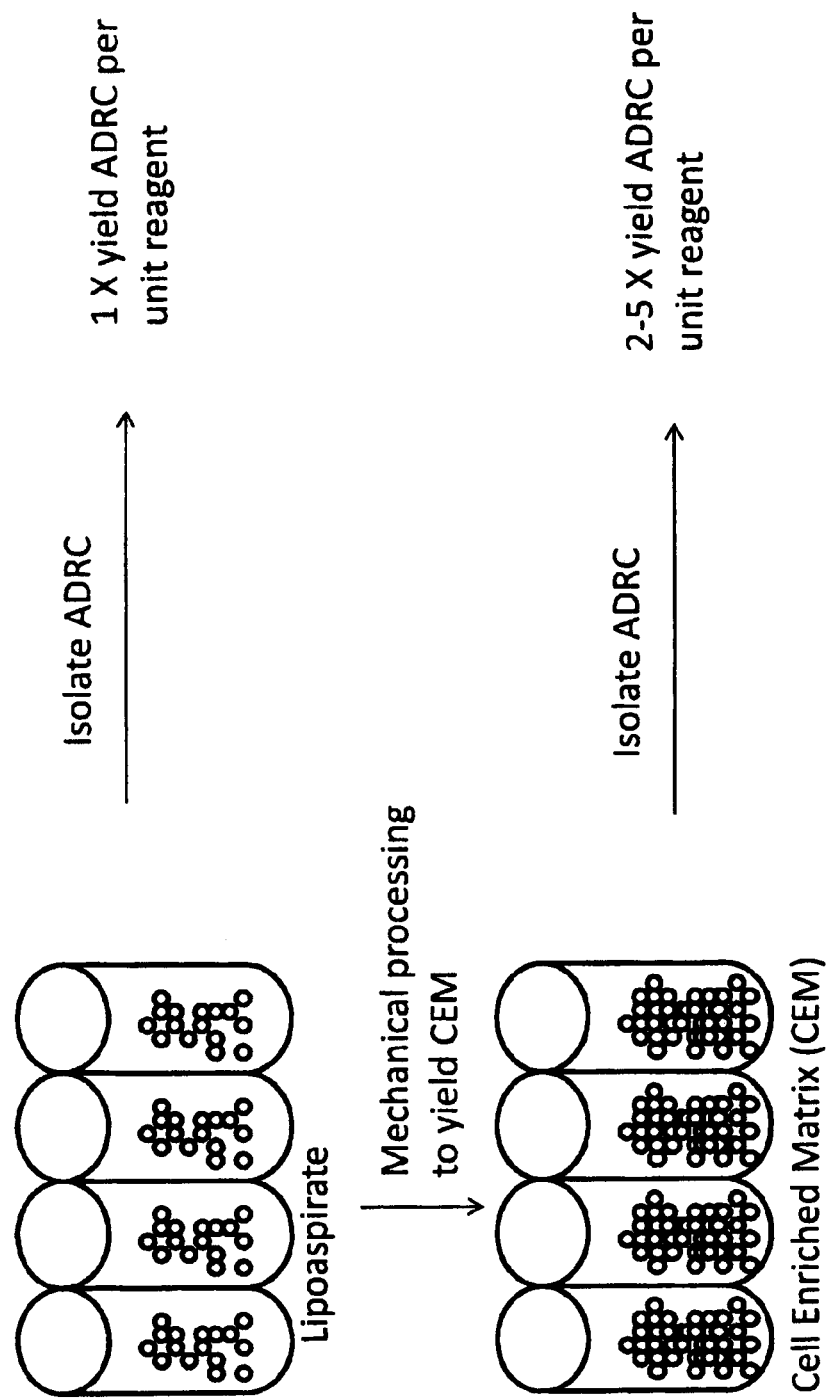
FIG. 15 is a schematic of a method to increase the efficiency of enzyme and disposable utilization in processing of adipose tissue or lipoaspirate to obtain ADRC. Tissue is first processed to concentrate ADRC in CEM, which is then combined and processed to yield ADRC.

FIG. 12 illustrates that a longer amount of time for centrifugation of the tissue sample yields a higher number of cell per gram of cell-enriched matrix. FIG. 13 illustrates that a 1200×g rate of acceleration yields a higher concentration of cells per cell-enriched matrix when compared to a 400×g rate of acceleration or no centrifugation at all.

Example 4

Fresh human lipoaspirate was divided into two aliquots. Aliquot 1 ("control method") was processed using conditions similar to those commonly employed in cosmetic surgery to prepare lipoaspirate derived fat graft. The lipoaspirate was centrifuged for 2 minutes at 200×g. Aliquot 2 ("cell-enriched matrix" (CEM) method) was processed by first extruding the lipoaspirate across a luer coupling between two syringes 5 times, and then centrifuging the extruded lipoaspirate for 30 minutes at 1200×g. After centrifugation, both methods resulted in fractionation into an upper oil layer, a middle tissue layer, and a lower aqueous layer. The middle tissue layer fraction of each aliquot was collected. A portion of the collected tissue layer fraction from each method was loaded into individual 1 cc syringes and administered subcutaneously into the nuchal area of female immunodeficient NU/NU mice (n=3 mice/preparation).

An additional portion of the tissue layer fraction from each method was processed at 37° C. with a blend of collagenases I and II and dispase, filtered through a 100 μm filter, and then centrifuged at 600×g to obtain the regenerative cells. Number of viable regenerative cells in the fresh cell preparations and number of plastic adherent cells in culture at 24 h were determined. At 1 month post-implantation, mice were sacrificed and grafts were evaluated.

Processing by the CEM method resulted in a 2.2 fold higher concentration of viable cells in the fresh preparation and a 5.5 fold higher concentration of plastic adherent cells compared to the control method. See Table 1. This cell enrichment translated to a higher viability of the graft at 1 month as evidenced by vascularization and absence of oil pockets in mice injected with the cell preparations obtained using the CEM method.

TABLE 1

| Method | Viable cells/g tissue | Adherent cells/g tissue |
| --- | --- | --- |
| Control | $2.82 \times 10^5$ | $5.35 \times 10^4$ |
| CEM | $6.16 \times 10^5$ | $2.94 \times 10^5$ |

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for recovering regenerative cells from a body tissue, comprising placing the body tissue together with at least a proteolytic enzyme in an aqueous medium in at least one container, and agitating the body tissue and enzyme by subjecting the container to repeated rounds of rotational acceleration and deceleration about an axis in a centrifuge for a predetermined period of time sufficient for said recovery, including maintaining the container inverted at an angle to said axis of rotation of the container during said repeated rounds of acceleration and deceleration thereof, said angle enabling agitation of said tissue and enzyme under conflicting centrifugal and gravitational forces.

2. The method of claim 1, including maintaining the container in a temperature controlled environment in a range from 26° C. to 42° C. during the repeated rounds of acceleration and deceleration.

3. The method of claim 1, wherein the body tissue is adipose tissue, and the proteolytic enzyme is at least one of a collagenase and a neutral protease.

4. The method of any of claims 1-3, wherein the body tissue is adipose tissue comprising regenerative cells located primarily in the vascular and perivascular space with the regenerative cells attached to lamina elastica interna, and aiding the regenerative cell recovery from the body tissue by use of the proteolytic enzyme as a combination of collagenase and at least one neutral protease.

5. A method for dissociating regenerative cells from a body tissue, comprising confining the body tissue together with at least one proteolytic enzyme in an aqueous fluid in a container to a level less than its full capacity, maintaining the container affixed angularly to a rotor of a centrifuge with one end of the container elevated relative to the other end thereof nearest the axis of rotation of the rotor, and agitating the contents of the container by applying rotational force to the rotor in a repetitive sequence of at least one start-stop round per minute to repetitively accelerate and decelerate the container rotationally about said rotor axis.

6. The method of claim 5, including controllably maintaining the temperature of the centrifuge interior during the repetitive acceleration and deceleration rounds of the container.

7. The method of claim 5, including collecting the dissociated regenerative cells after steps of at least washing and centrifugation following said repetitive sequence.

8. The method of any of claims 5-7, wherein the body tissue is adipose tissue, the proteolytic enzyme comprises a combination of collagenase and at least one neutral protease, and maintaining the interior of the centrifuge at a temperature in a range from 26° C. to 42° C. during agitation of the contents of the container.

9. The method of claim 5, wherein said body tissue is lipoaspirate.

10. The method of claim 9, further including maintaining a temperature in the range of from 26° C. to 42° C. inside said centrifuge while agitating the contents of said container.

11. The method of claim 5, including applying said rotational force to the rotor sufficient to produce centrifugal force in a range from about 50 g to about 4000 g on the container at times during the repetitive acceleration and deceleration rounds.

12. The method of claim 9, wherein said proteolytic enzyme is at least one of a collagenase and a neutral protease.

13. A method for recovering regenerative cells from a body tissue, comprising placing the body tissue together with at least a proteolytic enzyme in an aqueous medium in at least one container, and agitating the body tissue and enzyme by subjecting the container to repeated rounds of rotational acceleration and deceleration about an axis in a centrifuge for a predetermined period of time sufficient for said recovery, wherein the body tissue and the enzyme at least partially fill said container; and further including subjecting the resulting contents of said container to said repeated rounds of acceleration and deceleration using said rotational force applied to a rotatable shaft on which said container is maintained in a position such that gravitational force is directed opposite that of centrifugal force on said contents.

14. The method of claim 13, including detachably maintaining said container on a rotor on said rotatable shaft in said position at an upward inclination between a horizontal plane and a substantially vertical orientation of the shaft for rotation thereon, such that one end of the container is closer to the rotatable shaft and the opposite end thereof is elevated relative to said one end, rotating said container about said axis of the shaft at a rate of more than one round per minute of acceleration and deceleration, whereby to facilitate mixing of said contents, while maintaining the temperature of the interior of said centrifuge in a range between 26° C. and 42° C.

15. The method of claim 13, including applying said rotational force to produce said centrifugal force within a range from about 50 g to about 3000 g.

16. The method of claim 13, wherein the body tissue is lipoaspirate.

17. The method of claim 13, including utilizing multiple units of the container, each container having a proximal end into which the body tissue and enzyme are placed, and coupling the multiple containers angularly spaced apart to said rotatable shaft of the centrifuge such that one of the proximal end and the distal end of each container is coupled closest to the axis of rotation of the rotatable shaft and lies below its other end for the repeated rounds of rotational acceleration and deceleration on the rotatable shaft.

18. A method for processing a body tissue to recover cells therefrom, comprising introducing into a container the body tissue together with at least one proteolytic enzyme, detachably coupling the container radially to a rotor configurable to retain the container at one of (i) a fixed angle or (ii) an angle that varies with rotational force on the container, rotating the container under rotational forces through sequential rounds of acceleration and deceleration at a rate of at least one round per minute, and recovering cells from the body tissue as a combined result of conflicting centrifugal and gravitational forces on the container.

19. A method for dissociating regenerative cells from a body tissue, comprising loading the body tissue together at least one enzyme in an aqueous fluid in a container, and transmitting centrifugal forces to the contents of the container by rotating the container about a centrifuge axle in repeated rounds of acceleration and deceleration without decoupling the container from the axle or otherwise disturbing said contents between said repeated rounds, whereby to promote dissociation of the regenerative cells from the body tissue, including coupling an end of the container radially from and at an acute angle to said centrifuge axle for moving the contents of the container under centrifugal forces in a direction opposite their direction of movement under gravitational force.

* * * * *